US006569998B2

(12) United States Patent
Cummings et al.

(10) Patent No.: US 6,569,998 B2
(45) Date of Patent: *May 27, 2003

(54) SYNTHETIC GLYCOSULFOPEPTIDES AND METHODS OF SYNTHESIS THEREOF

(75) Inventors: Richard D. Cummings, Edmond, OK (US); Rodger P. McEver, Oklahoma City, OK (US)

(73) Assignee: Board of Regents of the University of Oklahoma

( * ) Notice: Subject to any disclaimer, the term of this patent is extended or adjusted under 35 U.S.C. 154(b) by 0 days.

This patent is subject to a terminal disclaimer.

(21) Appl. No.: 09/849,031

(22) Filed: May 4, 2001

(65) Prior Publication Data

US 2002/0026033 A1 Feb. 28, 2002

Related U.S. Application Data

(62) Division of application No. 09/334,013, filed on Jun. 15, 1999.
(60) Provisional application No. 60/089,472, filed on Jun. 16, 1998.

(51) Int. Cl.$^7$ .......................... C07H 3/06; A61K 31/70; A61K 38/14

(52) U.S. Cl. ........................ 530/395; 530/324; 530/325; 530/326; 530/327; 530/322; 530/333; 530/344; 530/402; 530/412; 514/25; 514/23; 514/42; 514/8

(58) Field of Search ..................... 530/395, 322, 530/324, 325, 326, 327, 333, 344, 402, 412; 514/23, 25, 42, 8

(56) References Cited

U.S. PATENT DOCUMENTS

| 5,047,335 A | 9/1991 | Paulson et al. ............. 435/69.1 |
| 5,180,674 A | 1/1993 | Roth .......................... 435/288 |
| 5,821,329 A | 10/1998 | Lobl et al. .................... 530/317 |
| 5,827,817 A | 10/1998 | Larsen et al. ................. 514/2 |
| 5,874,261 A | 2/1999 | Roth ........................... 435/97 |
| 5,929,036 A | 7/1999 | McEver |

FOREIGN PATENT DOCUMENTS

| EP | 0577580 | 1/1994 | |
| JP | 60197699 | * 10/1985 | ............ C07K/7/04 |
| WO | WO 94/11498 | 5/1994 | |
| WO | 9706176 | 2/1997 | |

OTHER PUBLICATIONS

Peters et al., Multiple–column solid–phase glycopeptide synthesis. J. Chem. Soc. Perkin Trans 1, 1163–1171.*

Leppanen et al., "Binding of Glycosulopeptides to P–selectin Requires Stereospecific Contributions of Individual Tyrosine Sulfate and Sugar Residues" J. Biol. Chem., (2000) 275 (50): 39569–39578.

Leppanen et al., "A Novel Glycosulfopeptide Binds to P–selectin and Inhibits Leukocyte Adhesion to P–selectin" J. Biol. Chem., (1999) 274 (35): 24838–24848.

Lo–Guidice et al., "Sialylation and Sulfation of the Carbodydrate Chains in Respiratory Mucins from a Patient with Cystic Fibrosis," J. Biol. Chem., (Jul. 1994) 269 (29): 18794–18813.

Wilkins et al., "Tyrosine Sulfation of P–selectin Glycoprotein Ligand–1 Is Required for High Affinity Binding to P–selectin," J. Blol. Chem., (1995) 270 (39) 22677–22680.

Amado et al., A Family of Human β3–galactosyltransferases, *J. Biol. Chem.*, (May 22, 1998) 273 (21): 12770–12778.

Atsushi et al., "Detection of protein–protein interactions in the nervous system using the two–hybrid system," *Trends in Neuroscience*, (1996) 19:261–266.

Bierhuizen et al., "Expression Cloning of a cDNA encoding UDP–GlcNAc:Galβ1–3–GalNAc–R (GlcNAc to GalNAc) β1–6GlcNAc transferase by Gene Transfer Into CHO Cells Expressing Polyoma Large Tumor Antigen," *Proc. Natl. Acad. Sci. USA*, 89:9326–9330, Oct. 1992.

Brockhausen et al. Control of O–glycan synthesis: specificity and inhibition of O–glycan core 1 UDP–galactose: N–acetylgalactosamine–α–R β3– galactosyltransferase from rat liver (1992), *Biochem, Cell Biol.*, 70: 99–108.

Brockhausen et al., "Enzymatic basis for sialyl–Tn expression in human colon cancer cells," *Glycoconjugate Journal*, (1998) 15:595–603.

Cheng et al., "Mucin Biosynthesis," (1982) *J. Biol. Chem.*, 257 (11): 6251–6258.

Delhom et al., "Synthesis of Sulfated Bioactive Peptides Using Immobilized Arylsulfotransferase from Eubacterium sp.," *Biotechnol. Lett.*, May 1996, vol. 18, No. 5, pp. 609–614, entire document.

(List continued on next page.)

*Primary Examiner*—Karen Cochrane Carlson
*Assistant Examiner*—Chih-Min Kam
(74) *Attorney, Agent, or Firm*—Dunlap, Codding & Rogers, P.C.

(57) ABSTRACT

A new class of synthetic glycosulfopeptides (GSPs) which have one or more sulfated tyrosine residues and a glycan linked to the peptide, the glycan preferably including a sialyl Lewis$^x$ group or a sialyl Lewis$^a$ group. In a preferred version the GSPs have an O-glycan comprising a β1,6 linkage to a GalNAc. The present invention further contemplates in vitro methods of the synthesis of these GSPs without the use of the cells and methods of their use in vivo as powerful anti-inflammatory antithrombotic, or anti-metastatic compounds. The invention also contemplates a method of synthesizing oligosaccharides by cleaving the glycan from the GSP.

13 Claims, 15 Drawing Sheets

OTHER PUBLICATIONS

Granovsky et al., "UDPgalactose: glycoprotein-N-acetyl-D-galactosamine 3-β3-D-galactosyltransferase activity synthesizing O-glycan core 1 is controlled by the amino acid sequence and glycosylation of glycopeptide substrates," *Euro. J. Biochem.*, (1994) 22:1039-1046.

Lopez et al., "o-Glycosylation potential of lepidopteran insect cell lines," *Biochimica et Biophysica Acta*, (1999) 1427:49-61.

Meier et al., "The ELAM LIgand Fucosyltransferase, ELFT, Directs E-Selectin Binding to a Secreted Scaffold Protein: A Method to Produce and Purify Large Quantities of Specific Carbohydrate Structures," *Chemical Abstracts*, XP-002124245, 119(17), 20/25/93.

Moore et al., "The P-Selectin Glycoprotein Ligand From Human Neutrophils Displays Sialylated, Fucosylated, O-Linked Poly-N-Acetyllactosamine," *The Journal of Biological Chemistry*, 269 (37):23318-23327, 1994.

Nishimune et al., "Detection of protein-protein interactions in the nervous system using the two-hybrid system," *Trends Neurosci.*, (1996) 19:261-266.

Pouyani et al.PSGL-1 Recvognition of P-Selectin is Controlled by a Tyrosine Sulfation Consensus at the PSGL-1 Amino Termiunus. *Cell*. Oct. 20, 1995, vol. 83, No. 2, pp. 333-343, entire document.

Sako et al. A sulfated Peptide Segment at the Amino Terminus of PSGL-1 is Critical for P-Selectin Binding. *Cell*. Oct. 20, 1995, vol. 83, No. 2, pp. 323-331, entire document.

Seitz et al., "Chemoenzymatic Solution- and Solid-Phase Synthesos of O- Glycopeptides of the Mucin Domain of MAdCAM-1, A General Route to O-LacNAc, O-Siayl-LacNAc and O-Sialyl-Lewis-X Peptides," *J. Am. Chem. Soc.*, 119:8766-8776, 1997.

Sueyoshi et al., "Expression of Distinct Fucosylated Oligosaccharides and Carbohydrate-Mediated Adhesion Efficiency Directed by Two Different α-1, 3-fucosyltransferases," *The Journal of Biological Chemistry*, 269(51): 32342-32350, 1994.

Thurnher et al., "T cell clones with normal or defective o-galactosylation from a patient with permanent mixed-field polyagglutinability," *Eur. J. Immunol.*, (1992) 22:1835-1842.

Wilkins et al., "Structures of the O-Glycans on P-Seletin Glycoprotein Ligand-1 from HL-60 Cells," *Journal Biol. Chem.* 2, Aug. 1996, vol. 271, No. 31, pp. 18732-18742, entire document.

Wünsch et al., "Synthesis of Cholecystokinin-Related Peptides and Their Biological Properties," *Biol. Chem. Hoppe-Seylor*, Apr. 1989, 370:317-321, entire document.

Yamamoto et al., "Chemoenzymatic Synthesis of a Novel Glycopeptide Using a Microbial Endoglycosidase," *Caro. Res.* Jan. 9, 1998, vol. 305, No. 3-4, pp. 415-422, entire document.

Copy of PCT International Search Report for PCT/US99/13455, Cummings et al., Jun. 15, 1999.

* cited by examiner

Effects on Neutrophils Adhesion to Immobilized Soluble P-Selectin

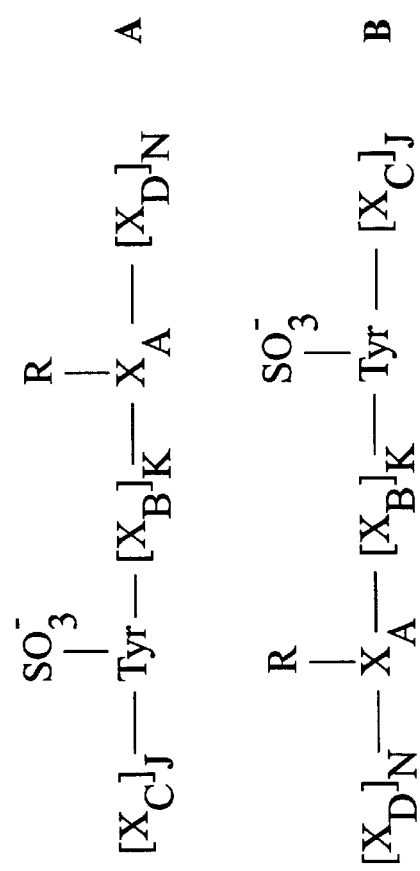
FIG. 7
FIG. 8
FIG. 9

SYNTHETIC GLYCOSULFOPEPTIDES AND METHODS OF SYNTHESIS THEREOF

CROSS-REFERENCE TO RELATED APPLICATIONS

The present application is a Divisional of U.S. Ser. No. 09/334,013, filed Jun. 15, 1999, which claims the benefit of U.S. Provisional Application Ser. No. 60/089,472, filed Jun. 16, 1998, which is hereby incorporated by reference herein in its entirety.

STATEMENT REGARDING FEDERALLY SPONSORED RESEARCH OR DEVELOPMENT

This work was supported in part by NIH grant POIHL 54804. The U.S. Government may have certain rights to this invention.

BACKGROUND

The present invention is directed to glycosulfopeptides, methods of their synthesis, and methods of their use in treating inflammation.

Inflammation is the reaction of vascularized tissue to local injury. This injury can have a variety of causes, including infections and direct physical injury. The inflammatory response can be considered beneficial, since without it, infections would go unchecked, wounds would never heal, and tissues and organs could be permanently damaged and death may ensue. However, the inflammatory response is also potentially harmful. Inflammation can generate pathology associated with rheumatoid arthritis, myocardial infarction, ischemic reperfusion injury, hypersensitivity reactions, and some types of fatal renal disease. The widespread problem of inflammatory diseases has fostered the development of many "anti-inflammatory" drugs. The ideal drug would be one that enhances the good effects resulting from the inflammatory response, and at the same time prevents the potentially harmful side-effects of this response.

The inflammatory response in regard to blood cells is accompanied by adhesion of circulating neutrophils, the most abundant phagocytic cell in the blood, to activated endothelial cells that line the vessels and make up the vessel walls. The adherent neutrophils are subsequently activated and the activated neutrophils emigrate from the blood into the surrounding tissue in a process termed diapedesis. The cells then begin engulfing microorganisms in a process termed phagocytosis and they also degranulate, releasing a variety of degradative enzymes, including proteolytic and oxidative enzymes into the surrounding extracellular environment. The mechanisms by which neutrophils adhere, become activated, and emigrate from the blood are currently major topics of research around the world. It is hoped that a fundamental understanding of these mechanisms will give rise to a new generation of anti- and pro-inflammatory drugs and treatments.

The initial attraction of circulating leukocytes to sites of inflammation is due to binding of the cells to a class of adhesion molecules termed selectins. The three currently identified selectins are L-selectin, which is constitutively expressed on the surfaces of all circulating leukocytes; E-selectin which is inducibly expressed on the surfaces of endothelial cells; and P-selectin, which is inducibly expressed on the surfaces of platelets and endothelial cells. The selectins recognize counter-receptors on other cells and thereby mediate cell-to-cell adhesive contacts. For example, P-selectin binds to a constitutively expressed, mucin-like glycoprotein counter-receptor on neutrophils termed the P-selectin glycoprotein ligand-1 (PSGL-1). the interaction between P-selectin and PSGL-1 promotes tethering and rolling adhesion of neutrophils on the vessel wall leading to neutrophil activation and eventual tight adhesion and diapedesis via integrins and their counter-receptors. Since it is well established that the selectin-mediated adhesion is an essential prelude to neutrophil activation and emigration during the inflammatory response, a tremendous amount of research has been done to identify compounds that inhibit neutrophil adhesion.

There have been attempts to use sialyl Lewis$^x$ mimetics to control or regulate the inflammatory response via inhibition of selectin-mediated adhesion [Lowe, "Therapeutic Inhibition of Carbohydrate-protein Interactions In Vivo," J. Clin. Invest., 100(11 Suppl):S47–51, 1997]. These are modified simple carbohydrates (<2,000 daltons) that contain the sialyl Lewis$^x$ or sialyl Lewis$^a$ antigen [Varki, "Sialic Acids As Ligands In Recognition Phenomena," FASEB. Journal, 11(4):248–55, 1997]. The sialyl Lewis$^x$ mimetics have been made as either free carbohydrates or as adduct between the carbohydrates and lipids to alter their solubility properties. Synthesis of these mimetics has been by one of two routes. In one common method the carbohydrate mimetics have been produced by entirely chemical steps beginning with commonly available precursors and organic chemical approaches. In the other common method the carbohydrate portions of the sialyl Lewis$^x$ mimetics have been synthesized primarily using recombinant or partly purified glycosyltransferases, including sialyltransferases, galactosyltransferases, fucosyltransferases and sugar nucleotide donors, such as cytosinemonophosphate sialic acid, uridinediphospho galactose and guanosinediphospho fucose. In all cases, the efficacy of these sialyl Lewis$^x$ mimetics has been poor and high doses (>0.5 mM) of the compounds are required, because they do not accurately reflect the structure of the appropriate selectin counter-receptor, e.g., PSGL-1, for P-selectin.

PSGL-1 on human leukocytes contains at its extreme amino terminus tyrosine residues that can potentially be sulfated and threonine residues that are potential binding sites for attachment of O-glycans containing N-acetylgalactosamine, N-acetylglucosamine, galactose, fucose and sialic acid with the sequence of the sialyl Lewis x antigen (McEver et al., "Leukocyte Trafficking Mediated by Selectin-Carbohydrate Interaction", J. of Biol. Chem., 270:11025–8, 1995. McEver et al., "Role of PSGL-1 Binding to Selectins in Leukocyte Recruitment", J. of Clin. Invest., 100:485–491, 1997).

The co-expression of sulfated tyrosine residues and the O-glycan appears to be required for high affinity interactions between PSGL-1 and P-selectin. However, naturally-occurring quantities of PSGL-1 are limited and it is not feasible to produce PSGL-1 from human neutrophils in a form suitable for administration as an anti-inflammatory compound. Moreover, recombinant means of synthesis of PSGL-1 are tedious and expensive and require animal cell culture and the consequent problems and uncertainties of proper post-translational modifications of the PSGL-1 peptide backbone, of which tyrosine sulfate and O-glycan addition are examples. It would be desirable to have a process which enables the formulation and production of compounds which overcome these problems.

DESCRIPTION OF THE DRAWINGS

In FIGS. 1A and 1B, glycosulfopeptide AcGP-1 is represented by SEQ ID NO:6, GP-1 by SEQ ID NO:7, GP-2 by SEQ ID NO:8, GP-3 by SEQ ID NO:9, GP-4 by SEQ ID NO:10, GP-5 by SEQ ID NO:11, GP-6 by SEQ ID NO:12, and GSP-6 by SEQ ID NO:13.

In FIGS. 2A and 2B, glycosulfopeptide P-1 is represented by SEQ ID NO:14, GP-1 by Seq ID NO:7, GP-2 by SEQ ID NO:8, GP-3 by SEQ ID NO:9, GP-4 by SEQ ID NO:10, GP-5 by SEQ ID NO:11, GP-6 by SEQ ID NO:12, and GSP-6 by SEQ ID NO:13.

In FIGS. 3A and 3B, glycosulfopeptide AcGSP-1 is represented by SEQ ID NO:15, GSP-1 by SEQ ID NO:16, GSP-2 by SEQ ID NO:17, GSP-3 by SEQ ID NO:18, GSP-4 by SEQ ID NO:19, GSP-5 by SEQ ID NO:20, and GSP-6 by SEQ ID NO:13.

In FIG. 4, glycosulfopeptide AcGSP-2-1 is represented by SEQ ID NO:21, GSP-2-1 is represented by SEQ ID NO:22, GSP-2-2 is represented by SEQ ID NO:23, GSP-2-3 is represented by SEQ ID NO:24, and GSP-2-4 is represented by SEQ ID NO:25.

FIG. 7 shows formulas of glycosulfopeptides contemplated by the present invention wherein the R groups represented are those in FIGS. 6A–6C.

FIG. 8 shows formulas of alternative embodiments of glycosulfopeptides contemplated by the present invention wherein the R groups are those represented in FIGS. 6A–C.

FIG. 9 shows formulas of additional alternative embodiments of glycosulfopeptides contemplated by the present invention wherein the R groups represented are those in FIGS. 6A–6C.

In FIGS. 10A and 10B glycosulfopeptide A is represented by SEQ ID NO:26, B by SEQ ID NO:27, C by SEQ ID NO:28, D by SEQ ID NO:29, E by SEQ ID NO:30, F by SEQ ID NO:31, G by SEQ ID NO:32, H by SEQ ID NO:33, I by SEQ ID NO:34, J by SEQ ID NO:35, K by SEQ ID NO:36, L by SEQ ID NO:37, M by SEQ ID NO:38 and N by SEQ ID NO:39.

DESCRIPTION OF THE INVENTION

The present invention contemplates a new class of synthetic glycosulfopeptides (GSPs) which mimic the extreme amino terminus of PSGL-1 in that they comprise one or more sulfated tyrosine residues and a glycan comprising a sialyl Lewis$^x$ group or a sialyl Lewis$^a$ group. In a preferred embodiment the GSPs further comprise an O-glycan comprising a β1,6 linkage to a GalNAc. The present invention further contemplates in vitro methods of the synthesis of these GSPs without the use of cells and methods of their use in vivo as powerful anti-inflammatory antithrombotic, or anti-metastatic compounds which are able to block the selectin-mediated adhesion of cells [Kim et al., "P-Selectin Deficiency Attenuates Tumor Growth and Metastasis," *Proc. Natl. Acad. Sci. USA*, 95(16):9325–30, 1998].

The glycosulfopeptides generated herein could not have been derived easily by expression of recombinant glycoproteins. Precise definition of the glycosylation and tyrosine sulfation in recombinant glycoproteins is exceedingly difficult, because of the inherent heterogeneity in glycan structures and the variable efficiency of tyrosine sulfation. Furthermore, cellular initiation of O-glycosylation by α-GalNAcT is complex. Each of the many different enzymes in this family may require a slightly different peptide motif for initiation of O-glycosylation in cells. The novel technology contemplated herein for synthesis of glycosulfopeptides allows the complete control of the O-glycan sites and structures without regard to O-glycosylation motifs. The in vitro synthesis of these glycosulfopeptides as contemplated herein also allows the introduction of modified monosaccharides, e.g., sialic acid derivatives, precise modifications of glycan structures, and modifications in the peptide length.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples, which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

Example 1

Figure 1A:
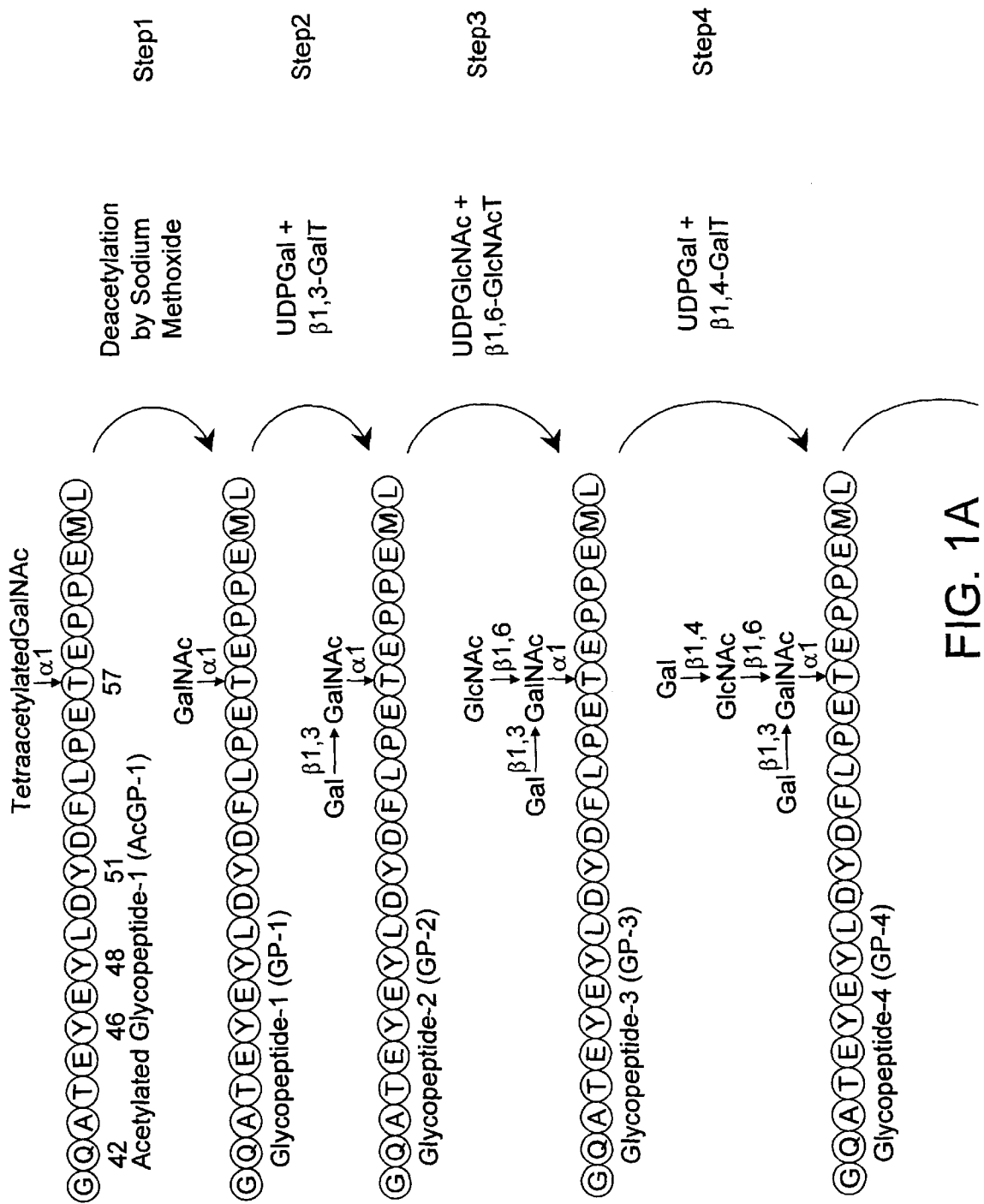
FIGS. 1A and 1B are a schematic which describes a method of synthesis of a glycosulfopeptide in accordance with the present invention.
Figure 1B:
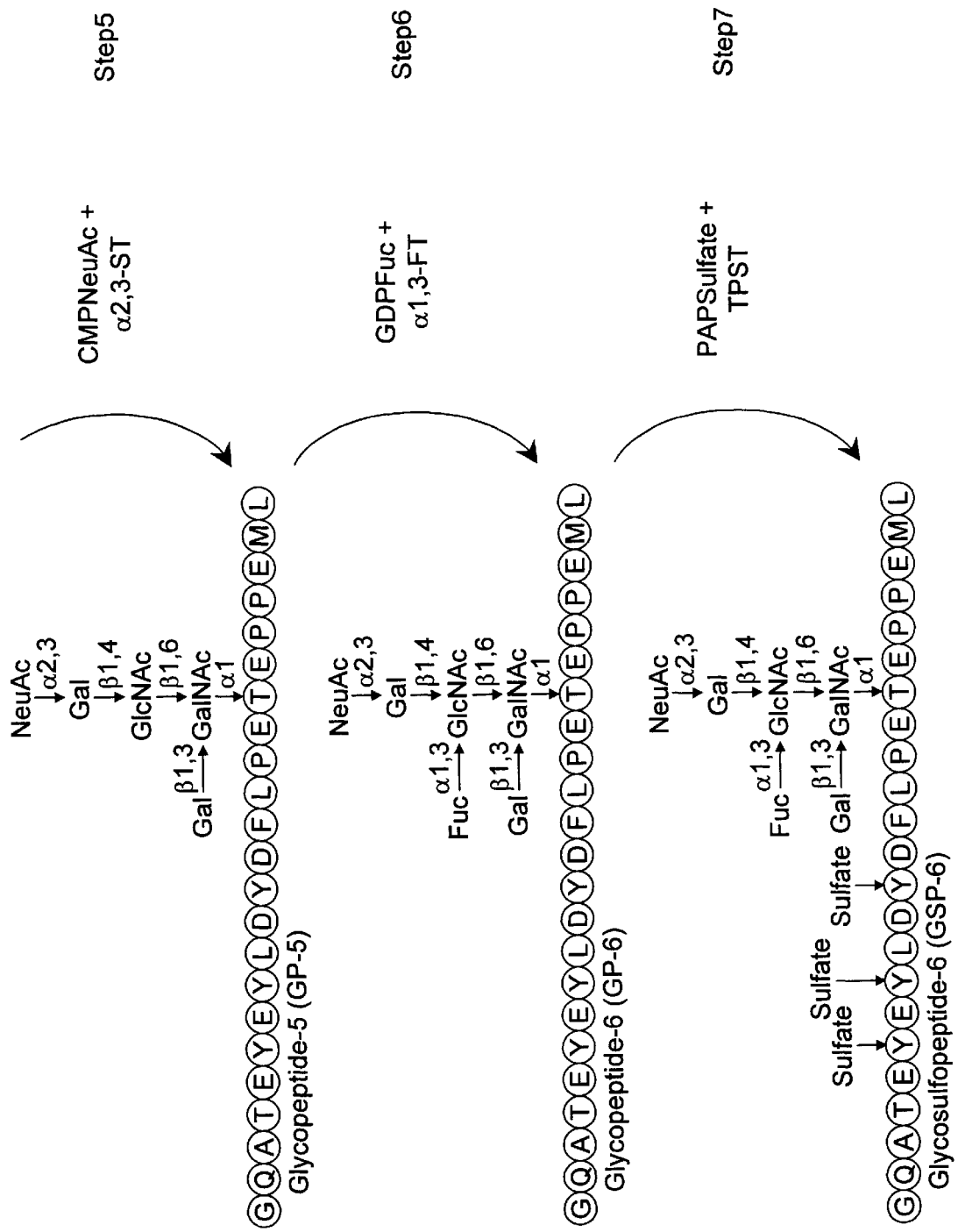
Figure 2A:
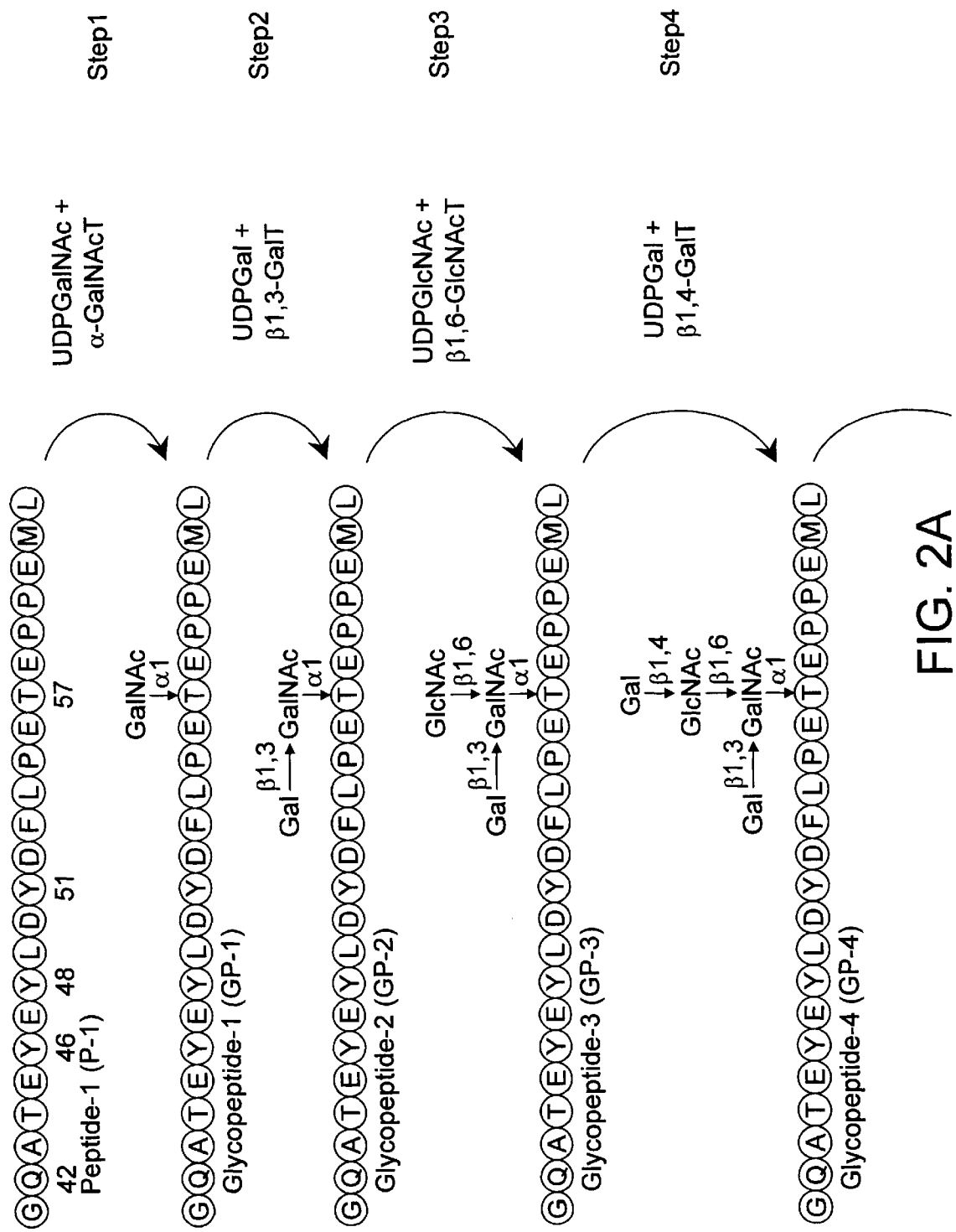
FIGS. 2A and 2B are a schematic which describes an alternate method of synthesis of a glycosulfopeptide in accordance with the present invention.
Figure 2B:
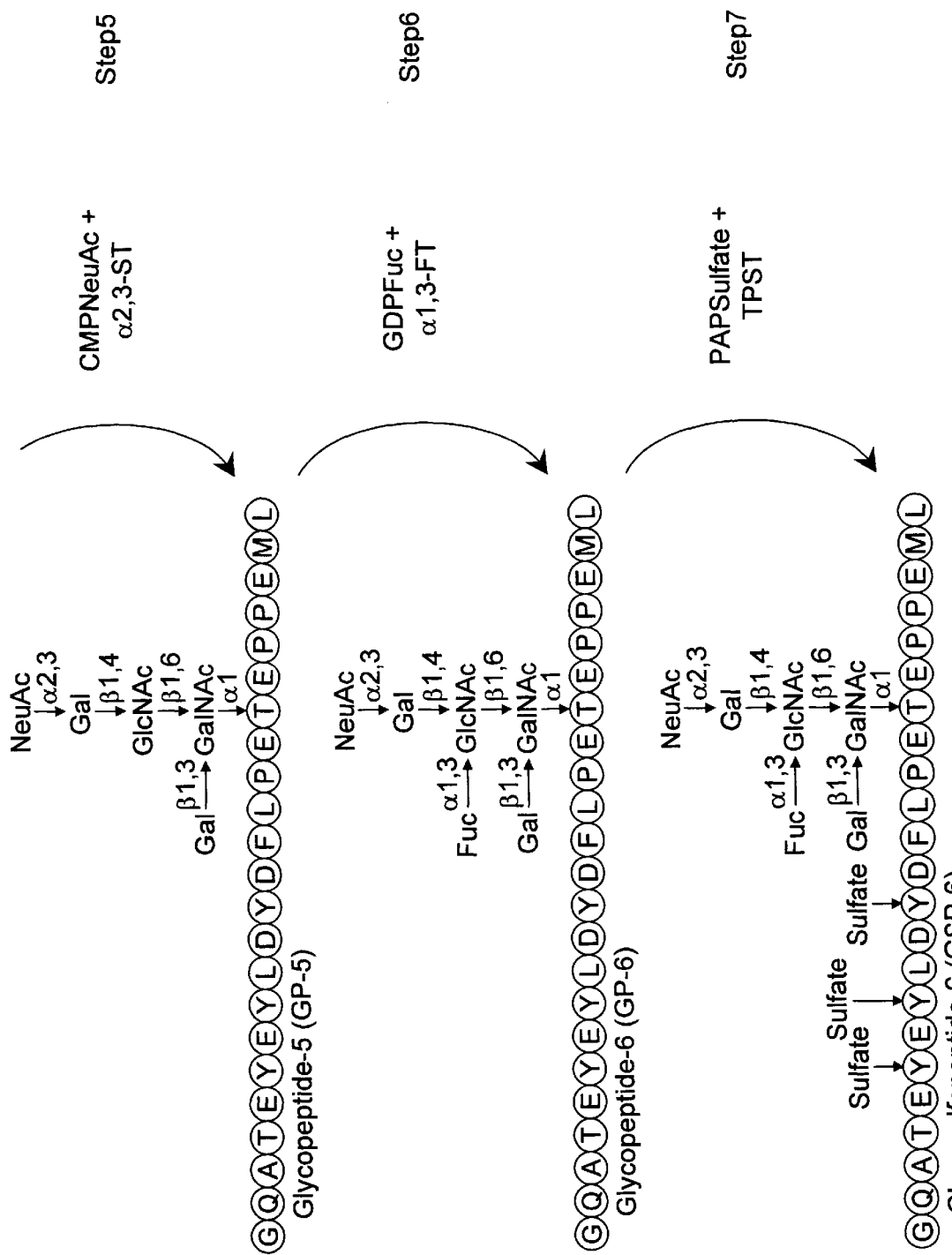

In one embodiment, represented in FIGS. 1A and 1B, the present invention contemplates glycosulfopeptides and a method of synthesis thereof by enzymatically adding sugars and sulfate groups to a presynthesized peptide comprising at least one tyrosine residue and at least one natural or synthetic amino acid residue able to provide an O-glycosidic linkage (e.g., serine, threonine, hydroxyproline, tyrosine, hydroxylysine, methionine). The peptide preferably comprises from two amino acids to 30 amino acids, and. more particularly may comprise from 3 to 29 amino acid residues, 4 to 28 amino acid residues, 5 to 27 amino acid residues, 6 to 26 amino acid residues, 7 to 25 amino acid residues, 8 to 24 amino acid residues, 9 to 23 amino acid residues, 10 to 22 amino acid residues, 11 to 21 amino acid residues, 12 to 20 amino acid residues, 13 to 19 amino acid residues, 14 to 18 amino acid residues, 15 to 17 amino acid residues, or 18 amino acid residues. In the exemplary peptide shown in FIGS. 1–4, 10, and 11, the amino acid sequence is the same as amino acids 42–63 of PSGL-1 except for an additional glycine residue added to the N-terminal end of residue 42.

The glycosulfopeptide preferably comprises at least one sulfated tyrosine residue, more preferably two sulfated tyrosine residues, and most preferably three sulfated tyrosine residues. Each tyrosine residue is preferably separated by at least one additional amino acid residue.

In this embodiment, the peptide is synthesized on a commercial peptide synthesizer using the f-moc or t-boc derivative of tetraacetylated GalNAc in a linkage to the hydroxyl group of the O-linking residue. This α-linked derivative of the O-linked amino acid is inserted at the desired position of the peptide during synthesis of the peptide thereby adding a tetraacetylated GalNAc with the O-linking residue.

The tetraacetylated GalNAc is then "unblocked" in step (1) by deacetylating with a weak base in organic solvent, such as sodium methoxide. The specific introduction of a GalNAc residue at the desired position ensures that the sugar-linked amino acid is present in quantitative and stoichiometric levels and that no other O-linked residue in another position in the peptide is modified.

In the next step (2), Gal is β-linked to the GalNAc via β1,3-GalT in the presence of UDPGal. In the next step (3), GlcNAc is β-linked t-o the GalNAc via β1,6-GlcNAcT in the presence of UDPGlcNAc. In the next step (4), Gal is β-linked to the GlcNAc via β1,4-GalT in the presence of UDPGal. In the next step (5), NeuAc is α-linked to the Gal via α2,3-ST in the presence of CMPNeuAc. In the next step (6), fucose is α-linked to the GlcNAc via α1,3-FT in the presence of GDPfucose. In the last step (7) of the synthesis, a sulfate group is added to each of the one or more tyrosine residues in the peptide via recombinant or at least partially purified TPST in presence of PAPsulfate. These steps are described in more detail in the experimental procedures section below. The result of the synthetic process in this embodiment is a peptide comprising a sulfated tyrosine and a sialyl Lewis$^x$ group having a β1,6 linkage to a GalNAc residue in O-linkage to a serine or threonine (or a similarly O-linkable amino acid). As noted above, in this embodiment, it is not possible to preferentially link a GalNAc to a specific threonine (or serine) residue (if there is more than one in the peptide) Further, although N-acetyl neuraminic acid is the preferred sialic acid to be used, other sialic acids which function in a similar manner are contemplated to be used in the glycosulfopeptides claimed herein. These alternative sialic acids include other sialic acids which can be transferred via the enzyme α2,3-ST, including N-glycolylneuraminic acid, N-acetylneuraminic acid, 9-0-acetyl-N-glycolylneuraminic acid, 9-0-acetyl-N-acetylneuraminic acid and other sialic acids described in Varki et al., "Sialic Acids As Ligands In Recognition Phenomena", *FASEB Journal,* 11(4):248–55, 1997, which is hereby incorporated by reference herein.

In this embodiment, it is also not possible to specifically sulfate only a particular tyrosine residue if the peptide comprises more than one tyrosine residue. Embodiments wherein it is possible to specifically sulfate particular tyrosine residues are described below.

A key to the abbreviations used herein is provided below.

Detailed Experimental Procedures

Synthesis of the Glycosulfopeptide of Example 1

Crude glycopeptide 1 (GP-1) was synthesized at the Protein Resource Facility of Oklahoma State University. Tri-O-acetylated GalNAc was incorporated into the peptide during the solid phase synthesis using tri-O-acetyl-GalNAcαFmoc Thr derivative (Oxford GlycoSciences, Oxford, UK). The crude GP-1 (2 mg) was de-O-acetylated with 6 mM methanolic sodium methylate as described in Medal et al., *Int. J. Peptide Protein Res.,* 43:529–536, 1994. The deacetylated peptide was purified by reversed phase HPLC. The retention time of deacetylated GP-1 (34.6 min) was clearly different from the tri-O-acetylated GP-1 (45.3 min). The yield of the pure GP-1 was 1.1–1.5 mg. In matrix-assisted laser desorption ionization time-of-flight (MALDI-TOF) mass spectra, the observed m/z for the [M-H]$^-$ molecular ion was 2952.9 (calc m/z 2953.2). In addition, the [M-H]$^-$ molecular ion of oxidized GP-1 (m/z 2969.5) was present where the methionine residue had been oxidized.

GP-1 was galactosylated overnight at 37° C. in 100–200 nmol aliquots by using 3–4 times molar excess of UDPGal (Sigma) and 13 nmol/h of purified core-1 β1,3-GalT (core-1 β1,3-galactosyl transferase) in a total volume of 100 μl of 50 mM MES, pH 6.5, 2 mM ATP, 15 mM MnCl$_2$, 0.2% Triton X-100. The complete amino acid sequence of core-1 β1,3-GalT is shown in SEQ ID NO:1. After removing proteins and Triton X-100 by chloroform-methanol (2:1) extraction (deproteination), the reaction mixture was analyzed by HPLC. The retention time of the galactosylated product, GP-2, was 32.9 min and the degree of galactosylation was >95%. MALDI-TOF analysis of GP-2 revealed m/z 3115.4 for the [M-H]$^-$ molecular ion (calc. m/z 3115.3).

GP-2 (0.4–0.6 mM) was incubated at 37° C. with 1–2 mM UDPGlcNAc (Sigma) and affinity purified recombinant core-2 β1,6-GlcNAcT (100 nmol/h) in a total volume of 100 μl of 50 mM Na-cacodylate, pH 7.0. A method for obtaining core-2β1,6-GlcNAcT is described below. After 24 h incubation a small aliquot from the reaction mixture was analyzed by HPLC. GP-2 was converted quantitatively into a faster moving product, GP-3 (retention time 31.3 min). MALDI-TOF mass spectrum of GP-3 showed m/z 3318.2 for the [M-H]$^-$ molecular ion (calc. m/z 3318.5). The reaction mixture was taken directly to a β1,4-GalT reaction. Alternatively, UDP[$^3$H]GlcNAc (American Radiolabeled Chemicals Inc., St. Louis, Mo.) (12,000 cpm/nmol) was used as a donor in the core-2 β1,6-GlcNAcT reaction to get [$^3$H]GP-3.

GP-3 (0.4 mM) (core-2 β1,6GlcNAcT reaction mixture) was galactosylated using 125 mU of bovine milk β1,4-GalT (Sigma) and UDPGal (1.5 mM) in a total volume of 160 μl of 40 mM Na-cacodylate, pH 7.0, 20 mM MnCl$_2$ and 0.02% NaN$_3$. After 20 h incubation at 37° C. a sample from the reaction mixture was analyzed by HPLC, which showed that all GP-3 had been converted into a faster moving product, GP-4 (retention time 30.4 min). In MALDI-TOF analysis the observed m/z for the [M-H]$^-$ molecular ion of GP-4 was 3480.4(calc. m/z 3480.7). Glycopeptide samples were deproteinated and desalted in a Sephadex G-50 column (10 ml, 0.7×25 cm) using water or 25 mM NH$_4$HCO$_3$ as an eluant. 0.5 ml fractions were collected and the glycopeptides were detected by measuring either UV absorbance at 215 nm or radioactivity of the fractions. After desalting and deproteination the sample was taken directly to an α2,3-sialylT reaction. Radiolabeled [$^3$H]GP-3 was galactosylated using UDP[$^3$H]Gal (Amersham, Buckinhamshire, England) (10, 000 cpm/nmol) as a donor.

GP-4 (1 mM) was s.ialylated using 20 mU of α2,3-(N)-sialylT (Calbiochem, La Jolla, Calif.) and 3 mM CMP-NeuAc (Sigma) in a total volume of 50 μl of 50 mM MOPS, pH 7.4, 0.1% BSA and 0.02% NaN$_3$. After 14 h incubation at 37° C. a 1 μg sample was analyzed by HPLC, which showed that GP-4 had been converted completely into a faster moving product, GP-5 (retention time 29.7 min). In MALDI-TOF analysis the observed m/z for the [M-H]⁻ molecular ion of GP-5 was 3770.6 (calc. m/z 3771.9). The reaction mixture was used directly for the α1,3-FucT reaction. Radiolabeled [³H]GP-4 (0.1 mM) was also sialylated using the donor CMP[³H]NeuAc (0.2 mM, 31,.500 cpm/nmol) (NEN, Boston, Mass.).

GP-5 (0.4 mM) was α1,3-fucosylated for 16 h at 37° C. with 2 mU of α1,3-FucT-VI (Calbiochem, La Jolla, Calif.) and GDPFuc (0.8 mM) (Calbiochem, La Jolla, Calif.) in a total volume of 120 μl of 50 mM MOPS, pH 7.4, 20 mM $MnCl_2$ and 0.02% $NaN_3$. A deproteinated and desalted sample was analyzed by HPLC which showed that GP-5 was converted completely into the product GP-6 (retention time 29.1 min). In MALDI-TOF analysis the observed m/z for the [M-H]⁻ molecular ion of GP-6 was 3917.5 (calc. m/z 3918.1). Starting with 185 μg of GP-2 the overall recovery of GP-6 was 88 μg, as determined by UV absorbance at 275 nm during the HPLC runs. Radiolabeled [³H]GP-4 was fucosylated using GDP[¹⁴C]Fuc (83,000 cpm/nmol) (Amersham) as the donor.

Several aliquots of GP-6 (0.02 mM) were sulfated for 35 h at 37° C. using 0.15 mM PAPS (Sigma) or [³⁵S]PAPS (NEN, Boston, Mass.) (specific activity 30300 cpm/nmol) and 0.85 nmol/h of recombinant human TPST-1 (SEQ ID NO:2). Alternatively, hTPST-2, (SEQ ID NO:3) could be used or any other functional tyrosylprotein sulfotransferase. The total reaction volume was 100 μl per aliquot in 40 mM PIPES, pH 7.0, 0.05 M NaCl, 0.1% Triton X-100 and 5 mM EDTA. After chloroform-methanol (2:1) extraction to remove protein and detergent, the reaction mixture was desalted by gel filtration and subjected toHPLC. The retention time of the product, GSP-6, was 15.6 min and the conversion of GP-6 to GSP-6 was >95%. Electrospray mass spectrum analysis showed the molecular mass of GSP-6 as 4158.0 (calc. 4159.2), confirming that three sulfate groups were present.

Alternatively, a radiolabeled form of GSP-6 was generated by incubating GP-6 (0.01 mM) for 14–17 h with 0.06 mM [³⁵S]PAPS (107,000–559,000 cpm/nmol) and 0.36 nmol/h of TPST-1 in a total volume of 50 μl. The conversion of GP-6 to ³⁵SO₃-GSP-6 was >85%. GP-2 (0.08 mM) was sulfated for 35 h at 37° C. by using 0.6 mM PAPS (Sigma) and 4.8 nmol/h of affinity purified recombinant TPST-1 in a total reaction volume of 400 μl. After deproteination and desalting the sample was analyzed by HPLC. The retention time of the product was 21.4 min and the conversion of GP-2 to GSP-2 was 98%. Electrospray mass spectra of GSP-2 showed the molecular mass as 3356.0 (calc. 3356.5), which confirmed that three sulfate groups were present. Alternatively, GP-2 (0.04 mM) was sulfated for 18 h at 37° C. using [³⁵S]PAPS (0.2 mM, 30300 cpm/nmol) (Sigma) and TPST-1 (0.7 nmol/h) in a total volume of 56 μl. The conversion of GP-2 to ³⁵SO₃-GSP-2 was >95%. GP-5 was sulfated in a similar fashion as GP-6 using [³⁵S]PAPS (30300 cpm/nmol) as a donor. The conversion of GP-5 to ³⁵SO₃-GSP-5 was >90%. The retention time of ³⁵SO₃-GSP-5 was 17.5 min in HPLC (not shown).

Reversed Phase High Performance Liquid Chromatography

Glycopeptide samples were filtered on a Spin-X membrane (Corning Costar, Cambridge, Mass.) and were subsequently analyzed in a reversed phase C-18 HPLC column (Vydac, Hesperia, Calif.) on a Beckman System Gold HPLC. The following solvent system was used at a flow rate of 1 ml/min: 1–10 min, 20% acetonitrile—80% water—0.1% TFA; 10–70 min, linear acetonitrile gradient from 20% to 45% in water—0.1% TFA; 10–70 min, linear acetonitril gradient from 20% to 45% in water—0.1% TFA. The UV absorbance at 215 nm or 275 nm was monitored and/or the radioactivity of the collected fractions was measured. The pooled fractions were dried under vacuum.

Equilibrium Gel Filtration Chromatography

Equilibrium gel filtration experiments were conducted in a Sephadex G-75 column (0.5×10 cm, 2 ml) equilibrated with 4 ml of 20 mM MOPS, pH 7.5, containing 150 mM NaCl, 2 mM $CaCl_2$, 2 mM $MgCl_2$, and 0.02% $NaN_3$ (buffer A), and ³⁵SO₃-GSP-6 (10,000 cpm/ml, specific activity 1700 cpm/pmol). Different amounts of soluble P-selectin (sPS) (25–1000 pmol) (Ushiyama et al., *J. Biol. Chem.*, 268:15229–15237, 1993) were preincubated for 30–60 min in 120 μl of buffer A containing ³⁵SO₃-GSP-6 and applied to the column. Samples were eluted with buffer A (including ³⁵SO₃-GSP-6), and 140 μl fractions were collected at a flow rate of 70 μl/min. Radioactivity in the fractions was determined by liquid scintillation counting. Control experiments to test inhibitors of binding between sPS and GSP-6 were performed using 400 pmol of sPS and 5,000 cpm/ml of ³⁵SO₃-GSP-6. The EDTA concentration was 1 mM in 20 mM MOPS, pH 7.5, 150 mM NaCl, 0.02% $NaN_3$. Anti-P-selectin monoclonal antibodies (G1 and S12) (8.00 pmol each) were preincubated for 30 min with sPS in buffer A before ³⁵So₃-GSP-6 was added. Elution was performed by using buffer A. with ³⁵SO₃-GSP-6.

P-selectin Affinity Chromatography

Soluble P-selectin was coupled to Ultralink™ Biosupport Medium (Pierce, Rockford, Ill.) according to manufacturer's instructions. P-selectin columns (0.8 ml, 0.6×2.7 cm) of different densities (0, 1.0, 1.3, 1.6, 2.0 mg/ml) were equilibrated with 25 ml of buffer A. Radiolabeled glyco(sulfo) peptides (800–1000 cpm, 1–10 cpm, 1–10 pmol) were dissolved in 200 μl of buffer A and applied to the sPS-columns. Bound material was eluted with Buffer B (20 mM MOPS, pH 7.5, containing 10 mM EDTA, 150 mM NaCl, 0.02% $NaN_3$). Fraction size was 0.5 ml and the flow rate was 200–250 μl/min. All fractions were counted for radioactivity.

Mass Spectrometric Analysis

Matrix-assisted laser desorption/ionization time-of-flight (MALDI-TOF) mass spectrometry was performed in the linear negative ion delayed extraction mode with a Biflex™ time-of-flight instrument (Bruker-Franzen Analytik, Germany) equipped with a nitrogen laser operating at 337 nm. HPLC purified glycopeptide samples, except GSP-2 and GSP-6, were dissolved in 30% aqueous acetonitrile, and a 0.5 μl aliquot (about 2.5 pmol) was mixed with 0.5 μl of 2,4,6-trihydroxyacetophenone matrix (3 mg/ml in acetonitrile/20 mM aqueous diammonium citrate, 1:1, by vol.) and immediately dried under reduced pressure. The spectra were externally calibrated with insulin [M-H]⁻ [M-2H]²⁻ signals. Electrospray ionization (ESI) mass spectra were collected in the negative ion mode using a Q-TOF hybrid quadrupole/orthogonal acceleration time-of-flight mass spectrometer (Micromass Ltd., UK). GSP-2 and GSP-6 were dissolved in 50% aqueous acetonitrile and injected into the mass spectrometer with a nanoelectrospray ion source. Instrument calibration was performed with sodium trifluoroacetate ion clusters.

Desialylation of GSP-6

³⁵SO₃-GSP-6 (6,000 cpm) was desialylated by treatment with 8.4 mU of *Arthrobacter ureafaciens* neuraminidase (Sigma) in 100 µl of 0.1 M sodium acetate pH 5.5 for 13 h at 37° C. The reaction mixture was desalted and deproteinated before analysis by chromatography on sPS-columns.

Construction, Expression and Purification of Recombinant, Soluble Core-2 β1,6-GlcNAcT A fusion protein was constructed that contained the catalytic and stem region of human core 2 β1,6-GlcNAcT with the 12-amino acid HPC4 epitope at both the N- and C-termini. The epitope is bound in a $Ca^{2+}$-dependent manner by the monoclonal antibody HPC4 [Rezaie et al., *Prot. Exp. Purif.*, 3:453–460, 1992]. The catalytic and stem region of the core 2 β1,6-GlcNAcT was amplified by PCR using a pcDNA3 plasmid containing the full length cDNA of the human core 2 β1,6-GlcNAcT (type L) as a template (Bierhizen et al., *Proc. Natl. Acad. Sci. USA*, 89:9326–9330, 1992). The following primers were used for amplification:

5' primer containing BamHI cleavage site, 5'-GCCTGA ATTTGTAAGGGATCCACACTTAGAGCTTGCTGGGG AGAATCC-3' (SEQ ID NO:4) and 3'-primer containing EcoRI site and HPC4 epitope, 5'-GTAGAATTC TTAT-CACTTGCCGTCGATCAGCCTGGGGTCCACCT GGTCCTCGTGTTTTAATGTCTCCAAAGC-3'(SEQ ID NO:5). The PCR product (1.2 kb) was cloned into pCR-TOPO 2.1 vector (Invitrogen, Carlsbad, Calif.) and used to transform *E. coli* strain JM109 for plasmid preparation. The construct was released from pCR-TOPO 2.1 vector by digestion with BamHI and Eco RV and purified by agarose gel electrophoresis. The construct (1.2 kb) was ligated into a BamHI/Eco RV site of modified pcDNA 3.1(+) vector (pcDNA 3.1 (+)TH) which contains an $NH_2$-terminal transferrin signal sequence and HPC4 epitope (Ouyang et al., *Proc. Natl. Acad. Sci USA*, 95:2896–2901, 1998) and used to transform *E. coli* strain DH5α. The resulting plasmid, pcDNA 3.1(+)TH-sC2 (6.7 kb), was isolated, sequenced and used to transfect CHO/dhfr⁻ cells using lipofectamine (Life Technologies, Inc.) Clonal selection was carried out under neomycin resistance, and the cells were maintained in low salt DME (Cellgro, Herndon, Va. containing 10% fetal calf serum and G418 (600 µg/ml). Stable clones of cells expressing core β1,6-GlcNAcT activity in the media (50 nmol/h/ml) were selected and grown to 100% confluency. The media was changed to low salt DME containing 2% fetal calf serum and incubated for 2–3 days. The media was collected and adjusted to 1 mM $CaCl_2$ and 5 mM benzamidine. Soluble core-2 β1,6-GlcNAcT containing an HPC4 epitope tag was purified from the conditioned medium (60 ml) using a HPC4-mAb affinity column (3.5 ml column of 5 mg/ml HPC4-mAb coupled to Ultralink™ Biosupport Medium) at 4° C. as described in Mehta et al., *Blood*, 90:2381–2389, 1997. The purified enzyme was stabilized by adding 0.1% BSA and the enzyme was concentrated using Centricon-30 ultrafiltration tubes (Amicon, Beverly, Mass.). The purified enzyme was used directly or aliquoted and stored at −20° C. The activity (8.2 µmol/h/ml) was stable at −20° C. for at least 2 months. Core-2 β1,6-GlcNAcT assays were performed using 1 mM Galβ1→3GalNAcα-pNp (Toronto Research Chemicals Inc., Canada) and 1 mM UDP-[³H] GlcNAc (specific activity 1000 cpm/nmol). The assays were carried out at 37° C. with 2.5–10 µl of the purified enzyme for 30 min or 25 µl of cell culture media for 2–3 h in a total volume of 50 µl of 50 mM Na-cacodylate, pH 7.0. The radiolabeled reaction product was separated from the radiolabeled donor using Sep Pak cartridges (Waters, Milford, Mass.).

Neutrophil Isolation and Labeling

Human neutrophils were isolated from healthy volunteers as described in Zimmerman et al., *J. Clin Invest.*, 76:2235–2246, 1985, and labeled with Calcein-AM (Molecular Probes, Inc., Eugene, Oreg.) according to the manufacturer's instructions.

Neutrophil Adhesion Assay

The adhesion assay was performed essentially as described in Ushiyama et al., *J. Biol. Chem.*, 268–15229–15237, 1993, with the following modifications. Calcein-labeled neutrophils were used. sPS was coated directly on wells of Immulon 1 microtiter plates by incubating the wells with 2 µg/ml of sPS in 0.1 M sodium carbonate buffer at 4° C. overnight (100 µl/well). For GSP-6 inhibition, the wells were preincubated with 50 µl of different dilutions of GSP-6 in HBSS containing 0.1% HSA at room temperature for 15 min. In control experiments, wells were preincubated with mAbs against P-selectin. In other controls, mabs against PSGL-1 or fluid-phase sPS were preincubated with 25 µl of the cell suspension at room temperature for 15 min. The neutrophils (25 µl) were then added to the sPS-coated wells. The number of adherent cells was quantified using an fmax fluorescence plate reader (Molecular Devices).

Example 2

In a second embodiment, the series of synthesis steps are the same as Example 1 except for the first step. In this embodiment of the invention, represented in FIGS. 2A and 2B, the presynthesized peptide (which comprises at least one tyrosine and at least one amino acid residue to which a glycan can be attached) is provided. The initially provided peptide of this embodiment lacks tyrosine residues which are sulfated and lacks a GalNAc linked thereto. The peptide which may be produced by a commercial peptide synthesizer is then exposed to a sequential series of sugar donors and corresponding sugar transferases to synthesize an oligosaccharide group linked to the O-linking residue of the peptide. In this example, the step (1) comprises exposing the peptide to UDPGalNAc in the presence of α-GalNAcT to add GalNAc in α-linkage to the serine or threonine residue (or other O-linking amino acid). If the peptide comprises more than one O-linking residue, in this method the GalNAc may or may not be added to only one of the O-linking residues. The subsequent steps are the same as for Example 1.

Example 3

Figure 3A:
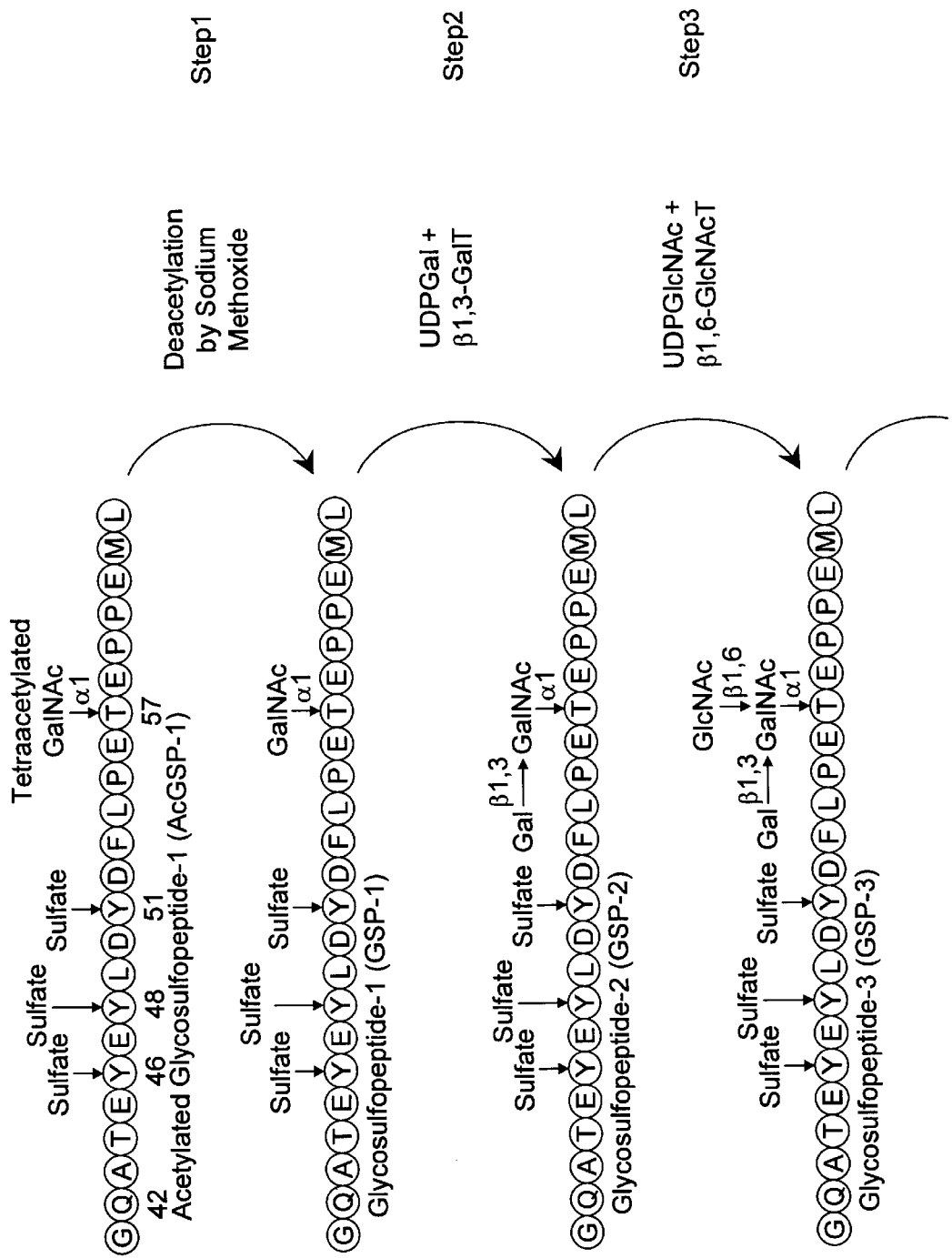
FIGS. 3A and 3B are a schematic which describes yet another alternate method of synthesis of a glycosulfopeptide in accordance with the present invention.
Figure 3B:
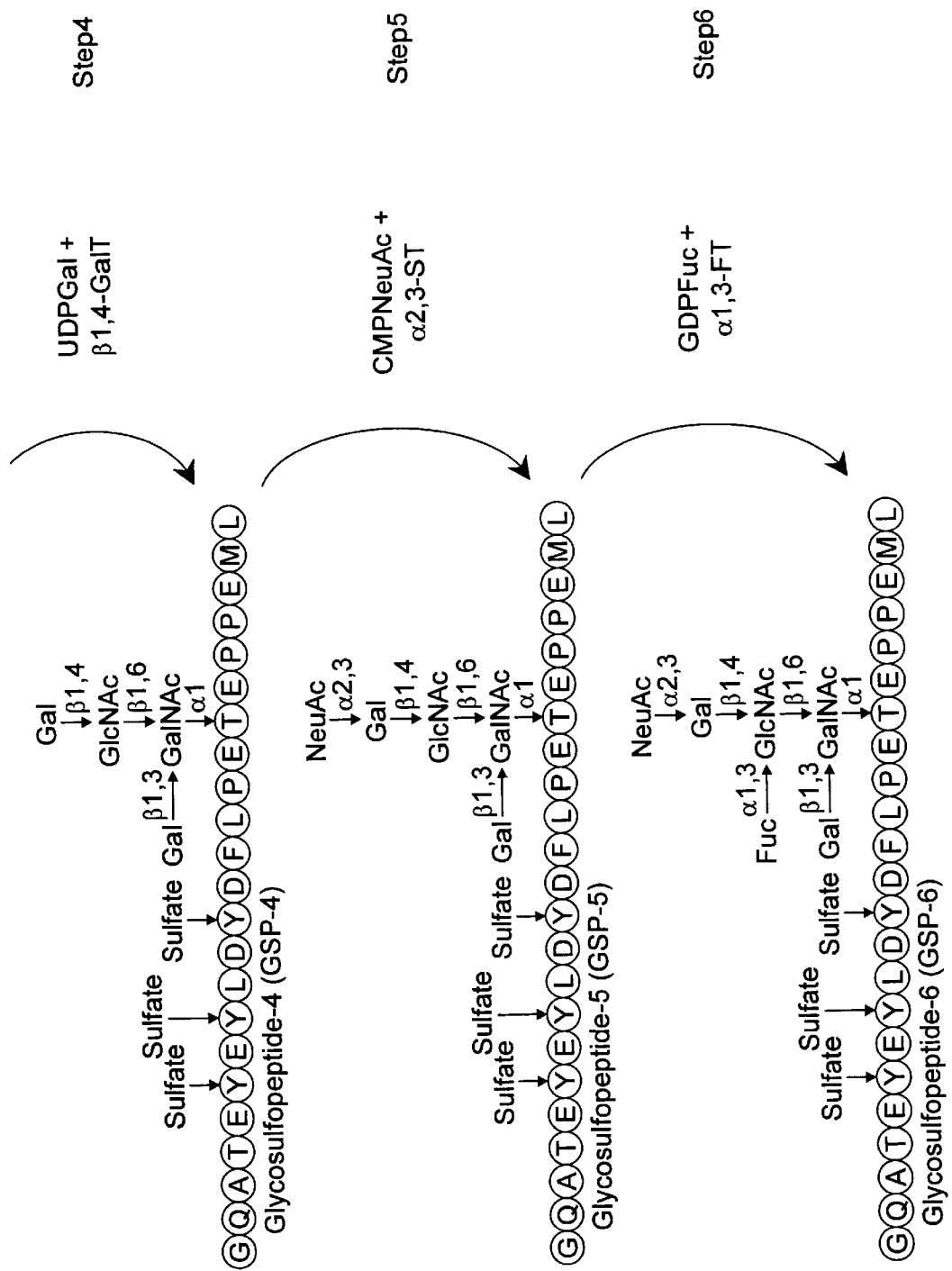

In an alternative embodiment, represented in FIGS. 3A and 3B, the peptide is created in the same manner as the peptide in Example 1 except for the sulfation step. In this embodiment, as the peptide is synthesized on a commercial peptide synthesizer, one or more sulfated f-moc or t-boc tyrosine derivatives are introduced into the synthesis cycle at appropriate stages to incorporate the tyrosine residues into the peptide at specific positions. Thus, before the oligosaccharide synthesis steps occur, the peptide has already been sulfated at the one or more tyrosine residues. The synthetic peptide with the one or more sulfated tyrosine residues is released under mild acid conditions to preserve the integrity of the sulfated tyrosine residues. The tetraacetylated GalNAc is unblocked as described above. The introduction of the tetraacetylated GalNAc residue at the specific position in the peptide ensures that no other O-linkage residue in the peptide is modified. The specific introduction of the sulfated tyrosines at one or more designated positions into the peptide assures that the one or more sulfated tyrosines are present in quantitative and stoichiometric levels.

Example 4

Figure 4:
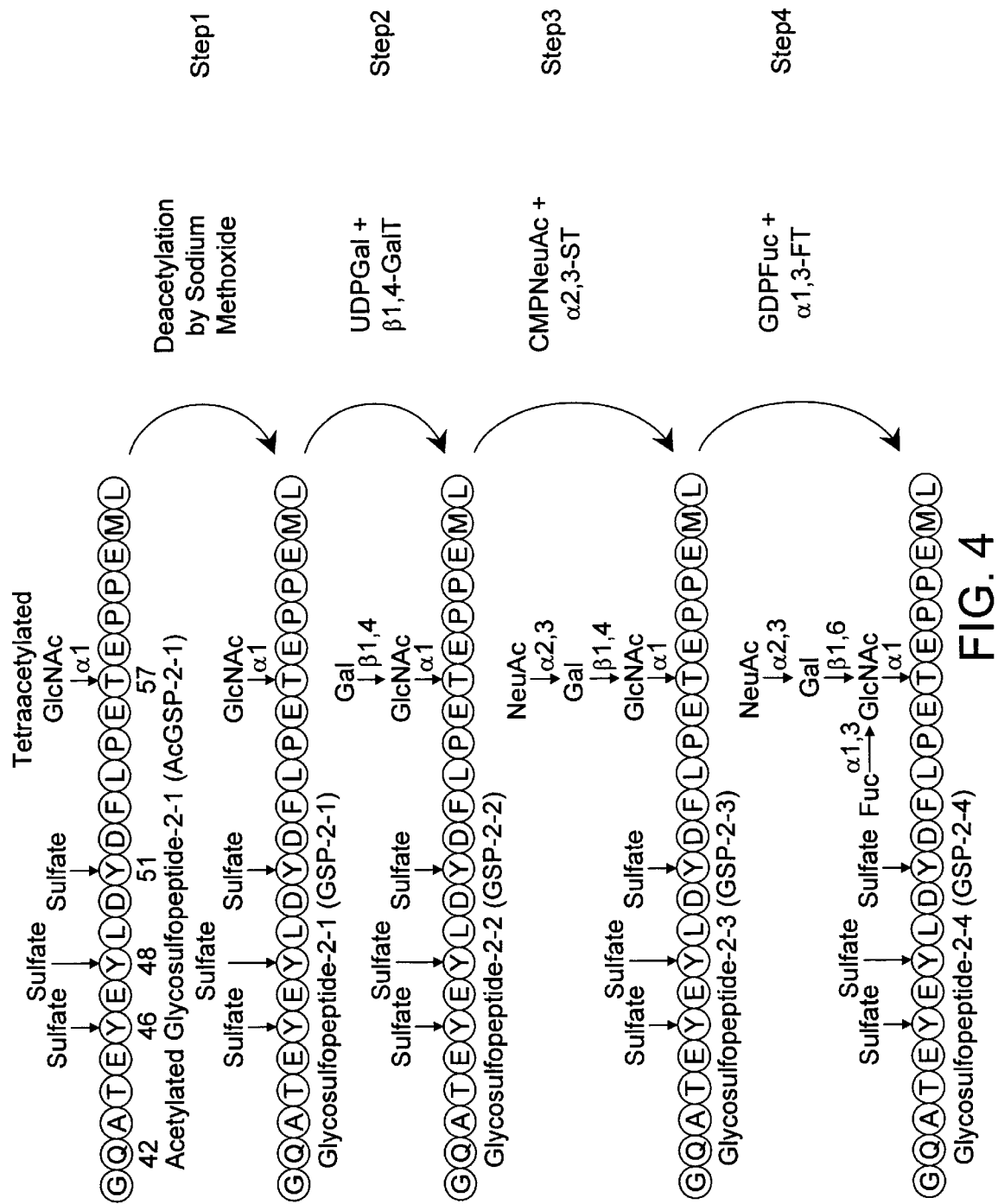
FIG. 4 is a schematic which describes yet another alternate method of synthesis of a glycosulfopeptide in accordance with the present invention.

In an alternative embodiment, represented in FIG. 4, the glycosulfopeptide may be constructed in the same manner as the glycosulfopeptide in Example 3 except the peptide may be initially synthesized using an f-moc-or t-boc derivative of tetraacetylated GlcNAc rather than a derivative of tetraacetylated GalNAc. In this embodiment, the O-glycan is constructed by deacetylating the peptide with a weak base in organic solvent such as sodium methoxide followed by steps 4–6 of Example 1 to add Gal, NeuAc and Fuc to the GlcNAc to create the O-glycan linked to the peptide. In this embodiment, the O-glycan is a sialyl Lewis$^x$ group O-linked directly to the O-linkable amino acid residue of the peptide.

Example 5

In an alternative embodiment a sulfate can be added to a specific tyrosine residue. The process shown in FIGS. 1A and 1B and described in Example 1 is duplicated except for the initial step and final step. In this embodiment, the peptide is initially synthesized using one or more phosphorylated tyrosine residues (Tyr-PO$_3^-$), for example, at the 46, 48 or 51 positions. The peptide is synthesized with at least one non-phosphorylated tyrosine residue, for example, at least one of the 46, 48, or 51 positions. The peptide therefore has at least one phosphorylated tyrosine residue and at least one non-phosphorylated residue.

This peptide is treated using the same steps described in Example 1, including treating the glycophosphopeptide with a tyrosylprotein sulfotransferase to add a sulfate group (SO$_3^-$) to the unoccupied tyrosine residue. The glycosulfophosphopeptide which results is then treated with alkaline phosphatase in a manner well known in the art. This treatment removes the phosphate groups from the tyrosines thereby leaving the sulfate group on the tyrosine to provide the final product, the glycosulfopeptide.

Examnle 6

To test whether a synthetic glycosulfopeptide of the present invention interacts with P-selectin, a series of affinity columns containing recombinant soluble P-selectin (sPS) at different coupling densities were prepared. The different column densities allow estimation of the relative affinities of synthetic glycosulfopeptides for P-selectin. A radiolabeled glycosulfopeptide having the same structure as glycosulfopeptide-6 (GSP-6) in FIG. 1 was applied to immobilized sPS in Ca$^{2+}$ containing buffer. The elution of the GSP-6 was retarded on columns containing 1.3 and 1.6 mg/ml sPS. The GSP-6 bound to the column containing 2.0 mg/ml sPS and could be eluted with EDTA. Other glycopeptides lacking the sulfates on tyrosines or glycosulfopeptides lacking the sLe$^x$ determinant had no detectable affinity for sPS. The results demonstrate the dual importance of sulfated tyrosines and sLe$^x$ for binding. Glycosulfopeptides lacking the fucosyl residue also did not bind detectably to immobilized sPS. These results demonstrate that both the sialic acid and the fucose in the sLe$^x$ group are necessary for high affinity binding of GSP-6 to immobilized sPS.

The dissociation constant (K$_d$) for binding of GSP-6 to soluble sPS was determined using an equilibrium gel filtration technique. Different amounts of fluid-phase sPS (25–1000 pmol) were loaded into small gel filtration columns equilibrated with $^{35}$SO$_3$-glycosulfopeptide-6 in Ca$^{2+}$-containing buffer. The binding data were plotted to derive the equilibrium binding constant, yielding an estimated K$_d$ of about 350 nM. Binding of GSP-6 to sPS was inhibited with EDTA and with the inhibitory anti-P-selectin mAb G1, which-binds to the lectin domain of P-selectin. Binding was not inhibited with anti-P-selectin mAb s12, which binds to one of the consensus repeats of P-selectin. These results demonstrate that GSP-6 binds with relatively high affinity to sPS in a Ca$^{2+}$-dependent manner.

Figure 5:
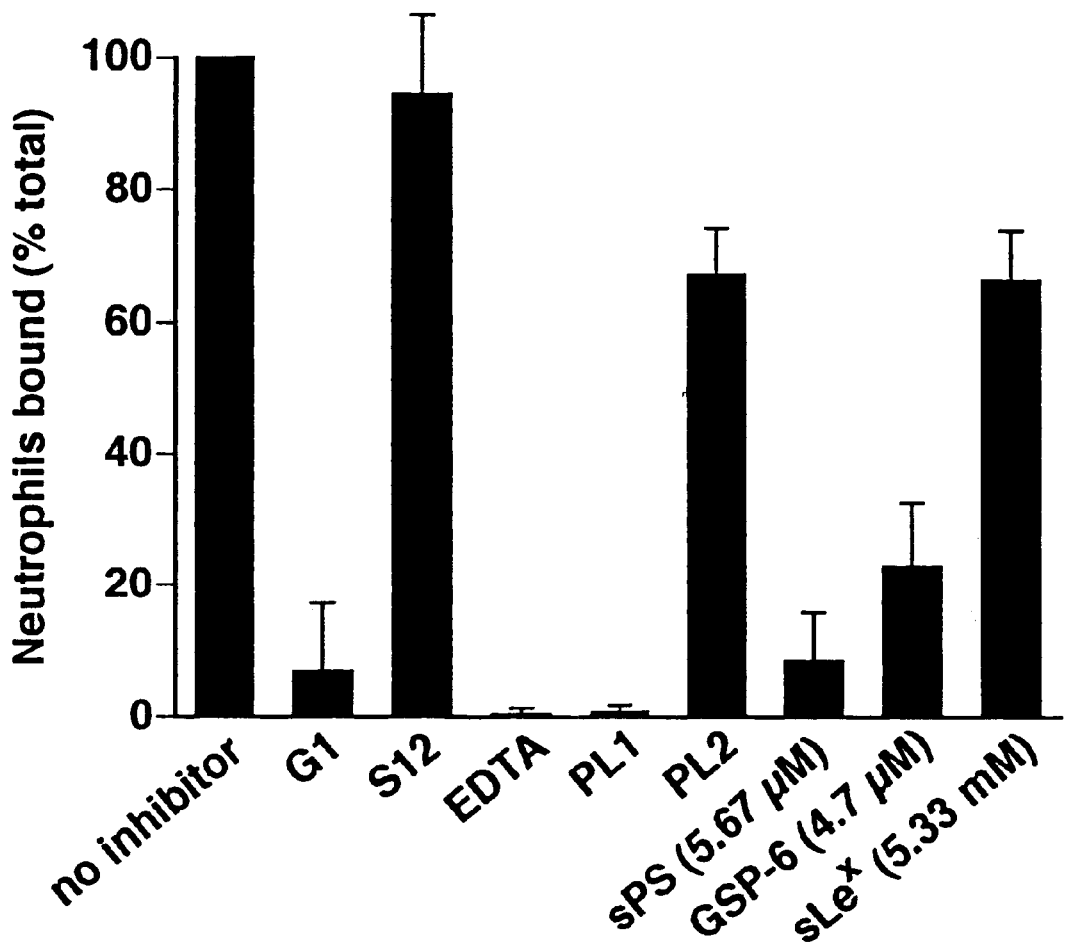
FIG. 5 is a graph showing the effects of various compounds on adhesion of neutrophils to immobilized soluble P-selectin.

The ability of GSP-6 to inhibit neutrophil adhesion to P-selectin was tested in microtiter wells coated with sPS (FIG. 5). First validated was the specificity of adhesion. Adhesion was inhibited by EDTA and the anti-P-selectin mAb G1, but not by the anti-P-selectin monoclonal antibody S12. Adhesion was also inhibited by PL1, a mAb directed to an N-terminal epitope of PSGL-1 that blocks binding of PSGL-1 to P-selectin. In contrast, PL2, which recognizes an epitope within the mucin decapeptide repeats of PSGL-1, did not inhibit adhesion. These results demonstrate that adhesion in this assay requires binding of PSGL-1 to sPS. Low concentrations of fluid-phase sPS (5.67 μM) inhibited neutrophil adhesion. A similar concentration of GSP-6 (4.7 μM) also significantly inhibited neutrophil adhesion to immobilized sPS. In marked contrast, a pure sLe$^x$-containing tetrasaccharide (NeuAcα2→3Galβ1→4[Fucα1→3]GlcNAc) only minimally inhibited neutrophil adhesion even at very high concentrations (5.3 mM). Taken together, these results demonstrate that GSP-6 binds specifically to P-selectin and strongly inhibits PSGL-1-dependent neutrophil adhesion to P-selectin.

Example 7

Figure 6A:
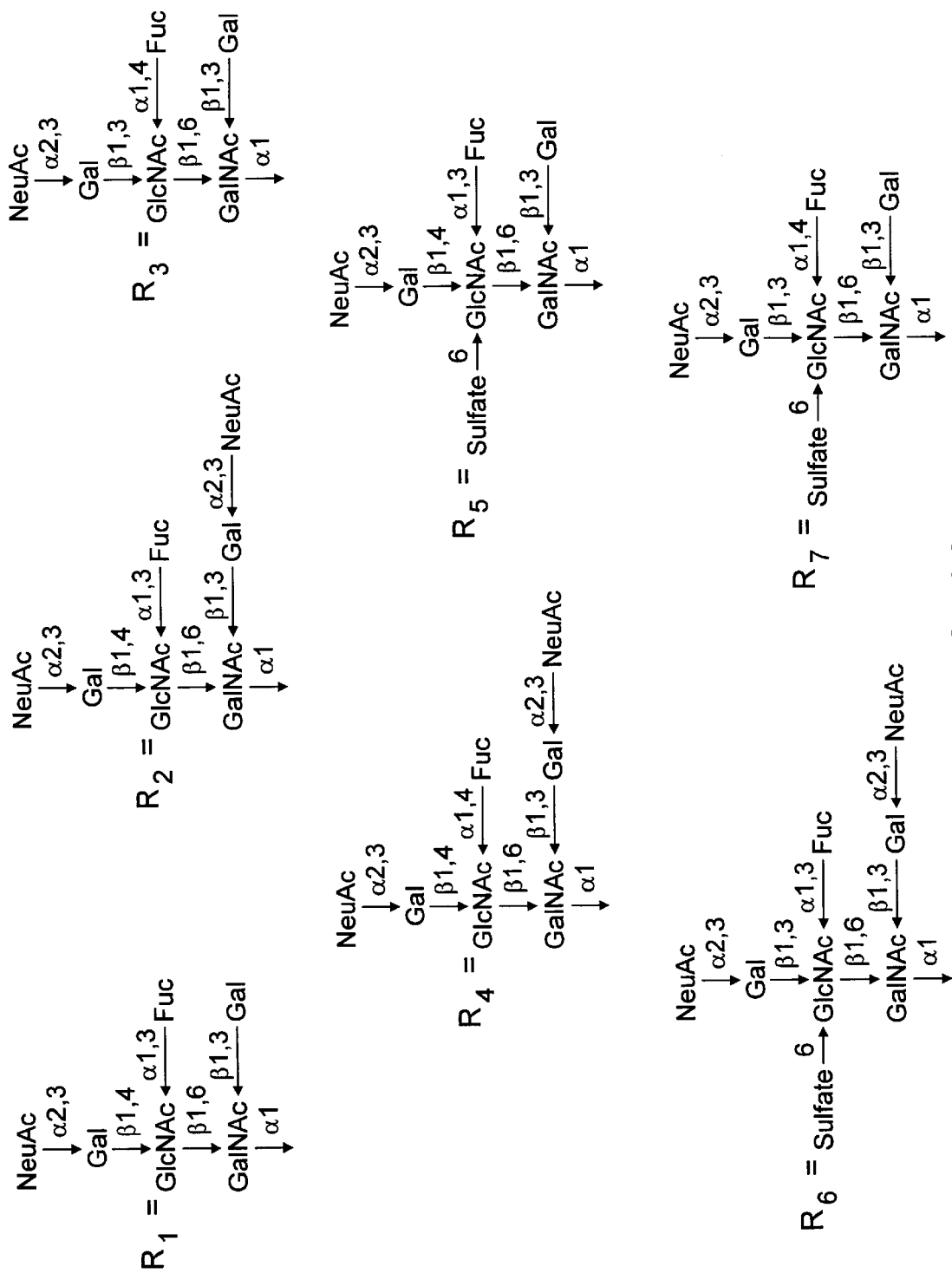
FIGS. 6A, 6B and 6C show chemical structures of a number of R groups among those which may comprise the O-glycan portion of the glycosulfopeptides contemplated by the present invention.
Figure 6B:
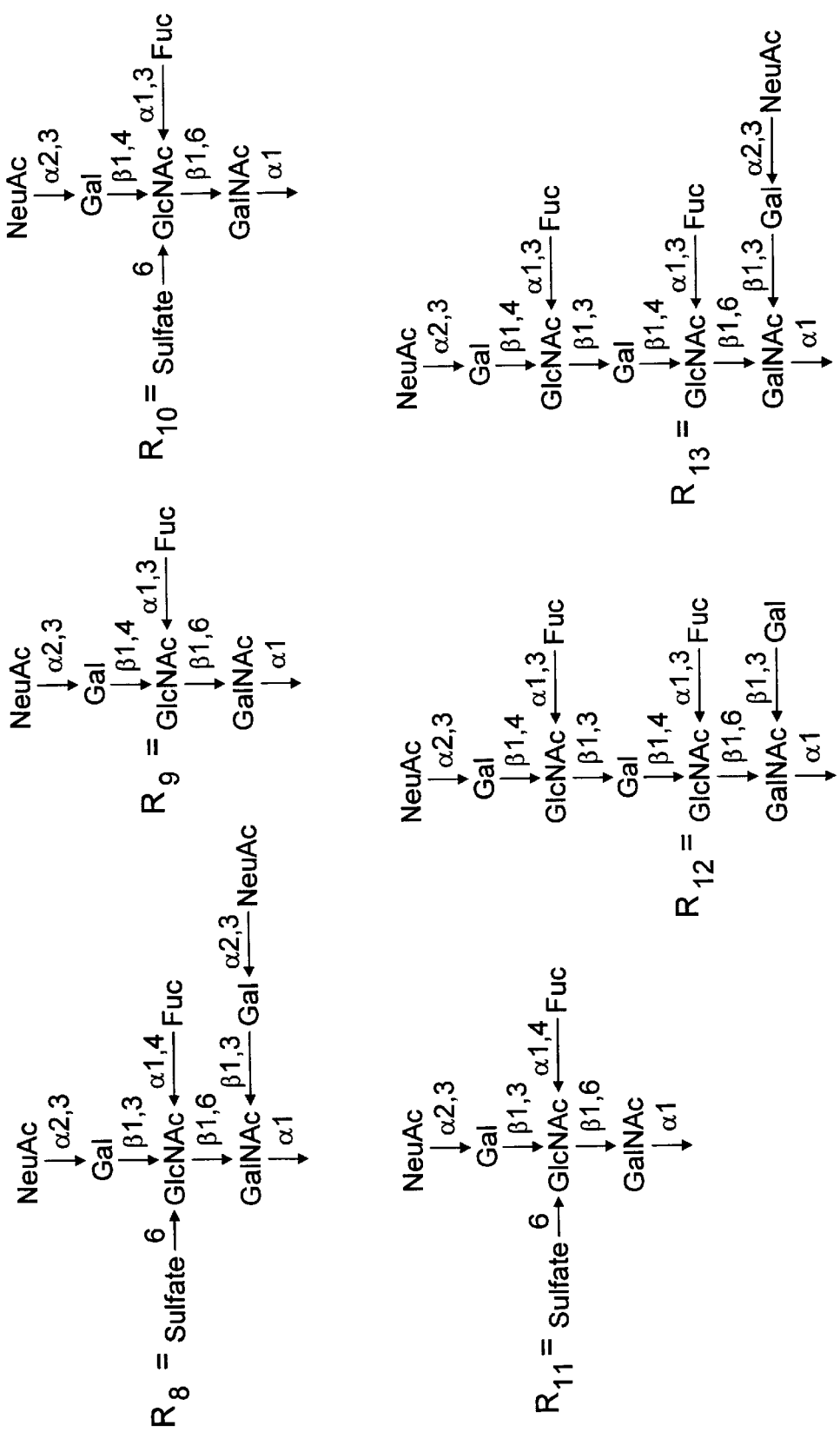
Figure 6C:
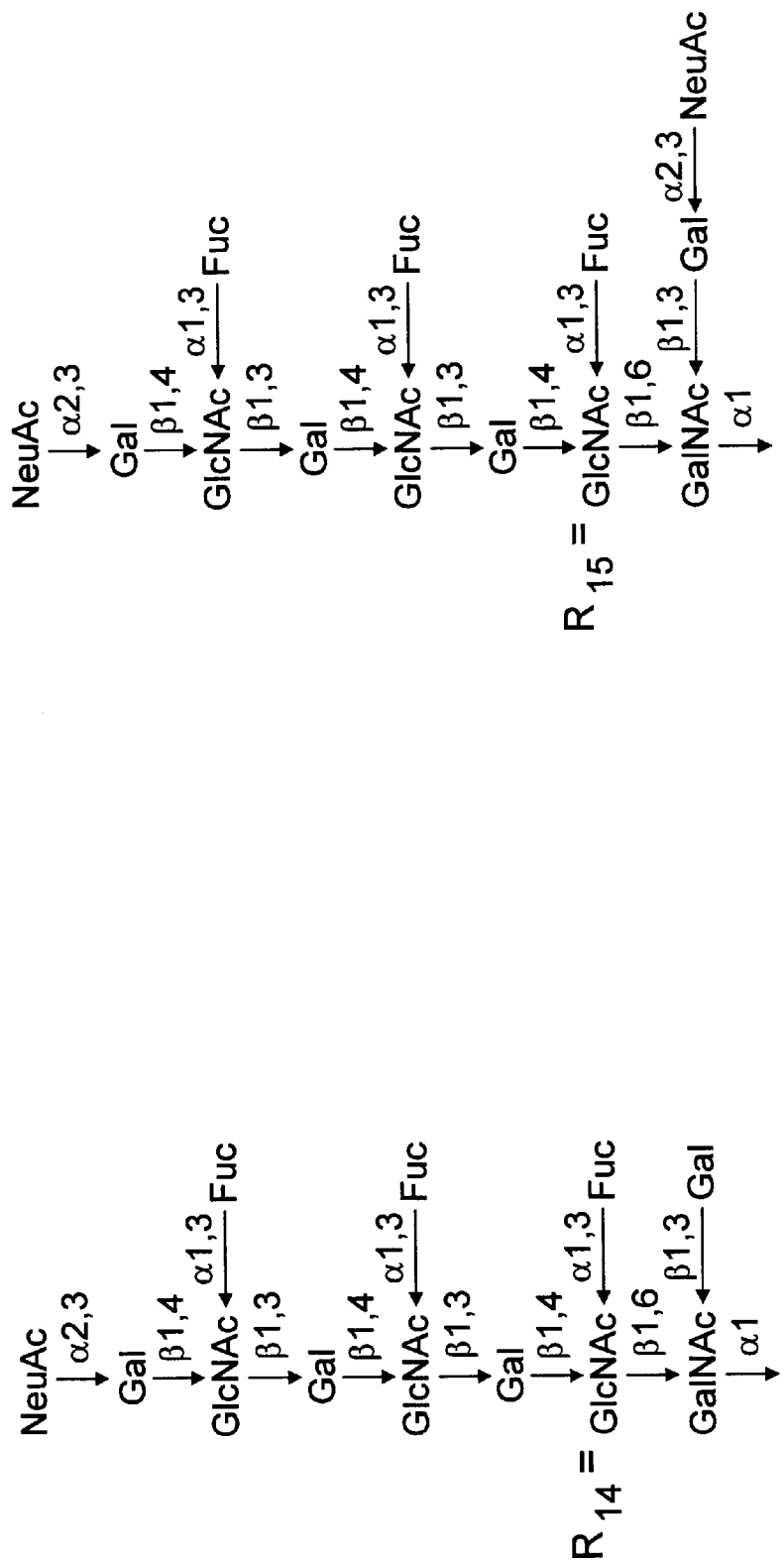

Examples of various oligosaccharide R groups which may comprise the O-glycan of the glycosulfopeptides contemplated herein are shown in FIGS. 6A, 6B and 6C. R$_1$ shown in FIG. 6A may be synthesized using the steps described in Example 1, for example.

R$_2$ is like R$_1$ except a NeuAc group has been added in an α2,3 linkage via α2,3-ST in the presence of CMPNeuAc to the Gal linked to the GalNAc.

R$_3$ is like R$_1$ except the Gal has been linked to the GlcNAc in a β1,3 linkage via β1,3-GalT and Fuc has been linked to the GlcNAc in an α1,4 linkage via α1,4-FT.

R$_4$ is like R$_3$ except a NeuAc group has been added in an α2,3 linkage via α2,3-ST in the presence of CMPNeuAc to the Gal linked to the GalNAc.

R$_5$, R$_6$, R$_7$ and R$_8$ are like R$_1$, R$_2$, R$_3$, and R$_4$, respectively, except a sulfate group has been linked to the GlcNAc.

R$_9$ and R$_{11}$ are like R$_1$ and R$_7$, respectively, except they are lacking a Gal in β1,3 linkage to the GalNAc.

R$_{10}$ is like R$_9$ but has a sulfate group linked to the GlcNAc.

R$_{12}$ is like R$_1$ but has a sialyl Lewis$^x$ group in β1,3 linkage to the terminal Gal group.

R$_{13}$ is like R$_{12}$ but has a NeuAc in α2,3 linkage to the Gal linked to the GalNAc.

R$_{14}$ is like R$_{12}$ except the terminal NeuAc is replaced with a sialyl Lewis$^x$ group in β1,3 linkage to the terminal Gal group.

R$_{15}$ is like R$_{14}$ but has a NeuAc in α2,3 linkage to the Gal linked to the GalNAc.

Groups R$_{14}$–R$_{15}$ are examples of O-glycans which may comprise the glycosulfopeptide contemplated herein. It will be understood, by a person of ordinary skill in the art that these R groups are only representative of the many O-glycans which may be used to synthesize the glycosulfopeptides of the present invention.

Example 8

As noted above, the present invention in its most basic form contemplates a dipeptide comprising a sulfate group linked to a first amino acid of the dipeptide and a glycan linked to a second amino acid, wherein the glycan is a sialyl Lewis$^x$ group or comprises a sialyl Lewis$^x$ group as a portion thereof. Preferably, the glycan is an O-glycan O-linked to the peptide. The first amino acid, to which the sulfate is attached, is tyrosine (Tyr). The second amino acid, to which the O-glycan is linked, is preferably a threonine (Thr) or serine (Ser) residue but may be any other amino acid residue to which an O-glycan can be linked in O-linkage (for example, tyrosine, hydroxyproline or hydroxylysine).

The present invention further contemplates that the glycan may be linked in N-linkage to the peptide via an amino acid such as aspartic acid, asparagine, glutamic acid, glutamine, arginine, lysine and cysteine. The present invention contemplates that the peptide may be covalently derivatized to contain the glycan. Examples of such dipeptides defined herein are shown in FIG. 7 as formulas A and B wherein $X_A$ represents a threonine, serine, or other residue to which the glycan may be linked, and R represents the R groups $R_1$–$R_5$ defined in Example 7 (and shown in FIGS. 6A–6C). R, of course, may be another O-glycan not shown in FIGS. 6A–6C if it enables the peptide to function in accordance with the present invention, i.e., binds with high affinity to P-selectin.

The present invention further contemplates peptides such as those represented as formulas A and B in FIG. 8. Glycosulfopeptides in FIG. 8 are similar to the glycosulfopeptides represented in FIG. 7 except one or more amino acid residues represented by $[X_B]_K$ may be disposed between the sulfate-linked residue (tyrosine) and the O-glycan linked residue $X_A$ (i.e., Ser, Thr or other O-linkable residue, natural or derivatized). $X_B$ represents any amino acid and k represents the number of amino acid residues $X_B$ in a sequence which, in a preferred embodiment, can be from 0–12. Where k=0, the peptides are those shown in FIG. 7. Where k=2 or more, the 2 or more residues which comprise $X_B$ may be the same amino acid or different amino acids.

A particularly preferred embodiment of the invention is shown below as Compound I, wherein the glycosulfdpeptide comprises a heptapeptide having a sulfated tyrosine residue at the N-terminal end and an O-glycosylated linking residue (such as Thr or Ser) at the C-terminal end of the peptide. The GSP comprises five intermediate amino acids represented as $X_1$, $X_2$, $X_3$, $X_4$, and $X_5$ as shown below. In one embodiment, $X_1$ is aspartic acid, $X_2$ is phenylalanine, $X_3$ is leucine, $X_4$ is proline and $X_5$ is glutamic acid. Preferably, the heptapeptide comprises a component (an amino acid or glycosyl component) which distinguishes it from a fragment of naturally-occurring or recombinantly expressed forms of PSGL-1, i.e., a fragment which could not be obtained from degradation of PSGL-1.

For example, the GSP may comprise fewer than seven amino acids wherein one or more of $X_1$–$X_5$ is not present. Alternatively, any one or more of $X_1$–$X_5$ may be substituted with a different amino acid, preferably one which has similar functional characteristics as the amino acid being substituted for. Alternatively, $X_1$–$X_5$ may comprise repeats of the same amino acid, e.g., five glycine residues. In an especially preferred version the peptide contains one proline residue in the position between tyrosine and the O-linking residue to which the glycan is linked.

(I)

NeuAc
↓ α2, 3
Gal
↓ β1, 4
Fuc —α1, 3→ GlcNAc
↓ β1, 6
SO$_3^-$— Gal —β1, 3→ GalNAc
|                    |α1
Tyr-X$_1$-X$_2$-X$_3$-X$_4$-X$_5$-(O-linking aa, e.g., Thr or Ser)

Example 9

The glycosulfopeptides represented by formulas A and B in FIG. 9 are essentially the same as glycosulfopeptides in FIG. 8 except each peptide may be extended in an N-terminal and/or C-terminal direction (A and B, FIG. 9, respectively) by j or n additional amino acid residues $[X_c]$ and/or $[X_D]$, respectively, where j and n may be, in a preferred version of the invention, from 0–12, and where $[X_c]$ and $[X_D]$ may represent any amino acid. For example, $X_c$ or $X_D$ may each comprise one or more amino acids which are the same, or may comprise different amino acids.

Figure 10A:
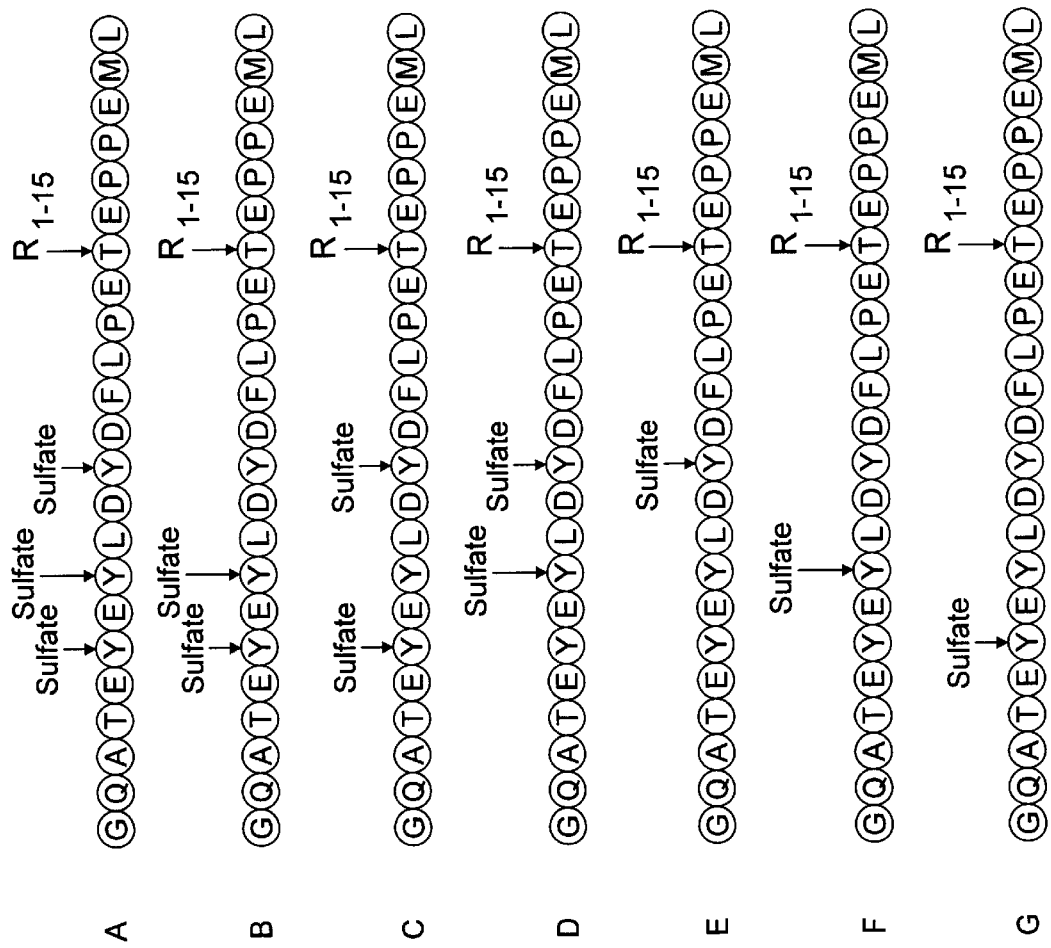
FIGS. 10A and 10B shows specific amino acid sequences for a number of glycosulfopeptides contemplated herein, where the glycosulfopeptides may comprise from one to three sulfates and R groups $R_1$–$R_{15}$ as defined in FIGS. 6A–6C.
Figure 10B:
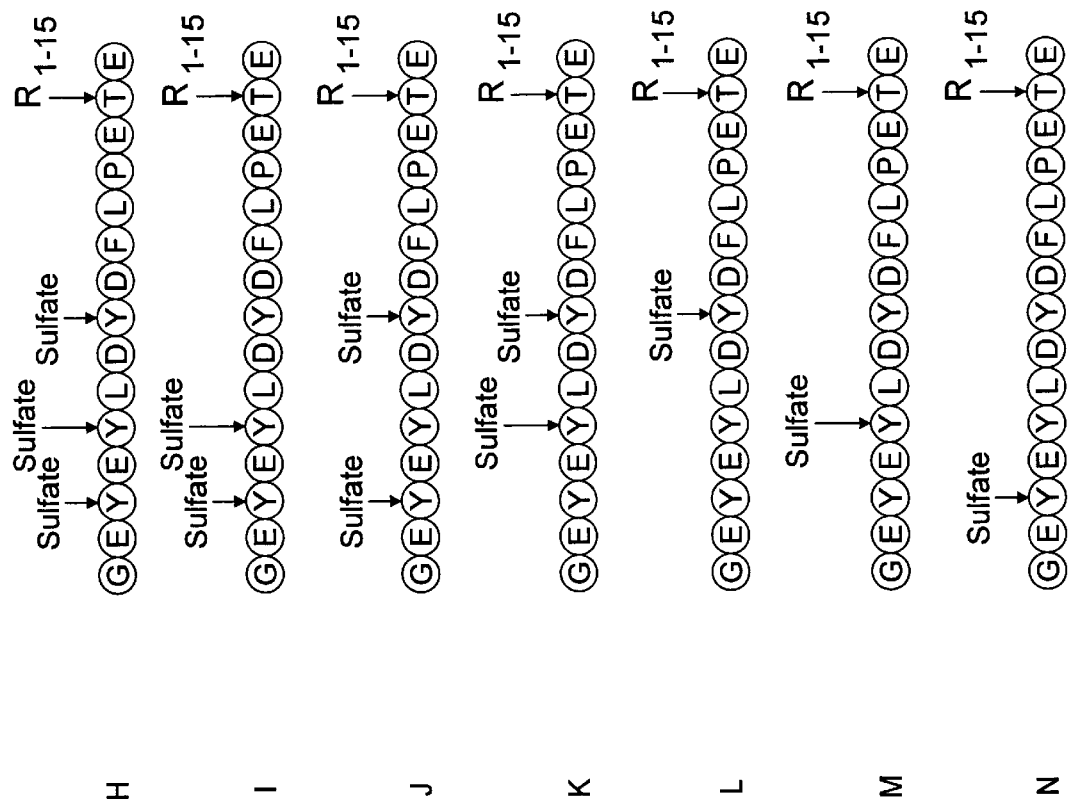
Figure 11:
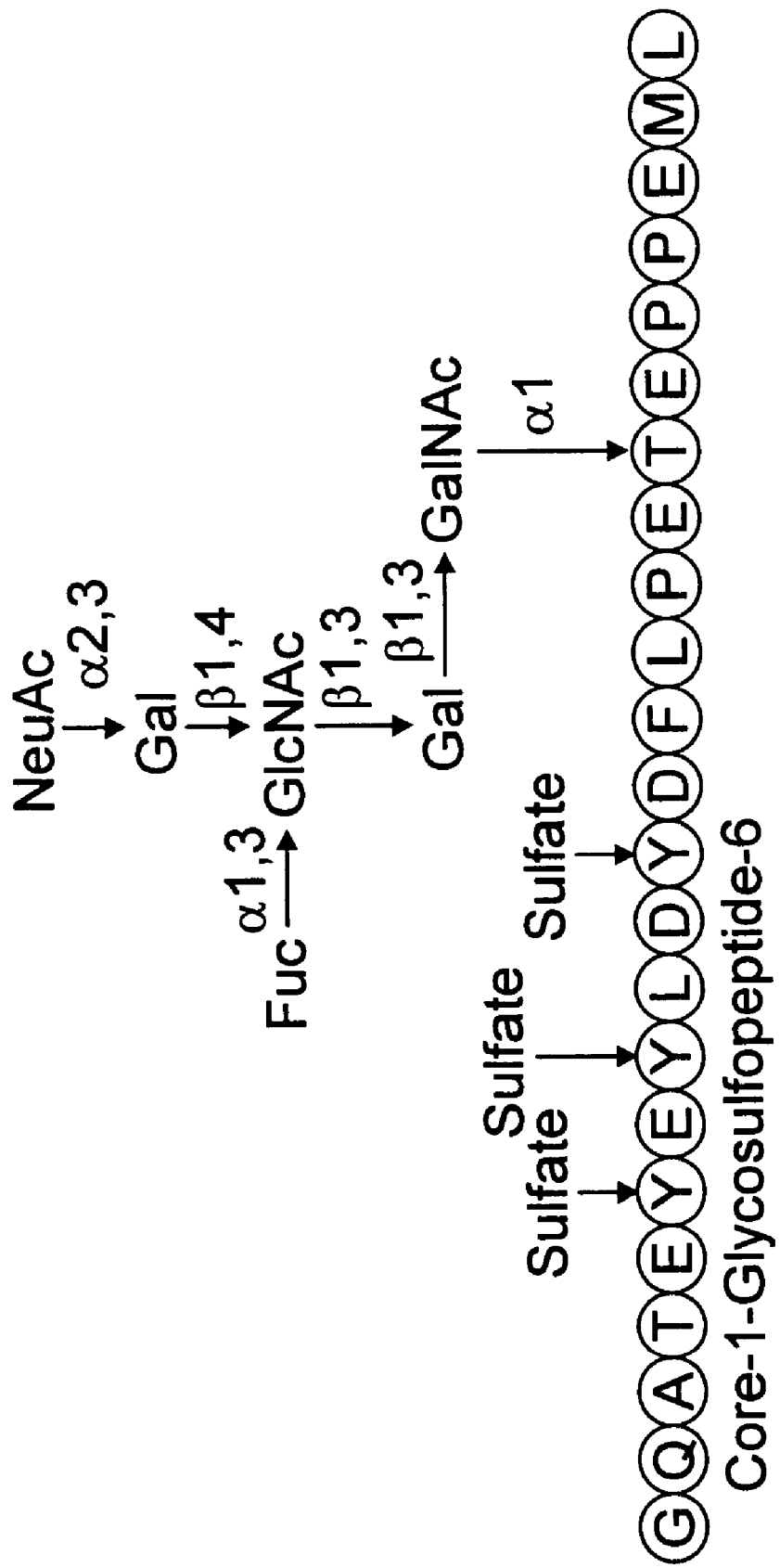
FIG. 11 shows a formula of a glycosulfopeptide comprising a core-1 O-glycan. Core-1 glycosulfopeptide-6 is represented by SEQ ID NO:40.

Further, it is contemplated herein that the glycosulfopeptide may comprise more than one sulfated tyrosine residue as shown in FIGS. 10A and 10B. FIGS. 10A–B show a number of preferred glycosulfopeptides A–N having one, two, or three sulfated tyrosine residues. Glycosulfopeptides A and H, for example, comprise three tyrosine residues each having a sulfate group linked thereto. Glycosulfopeptides B, C, D, I, J, and K each have two sulfated tyrosine residues. Glycosulfopeptides E, F, G, L, M, and N, each have one sulfated tyrosine group. The glycosulfopeptides represented in FIGS. 10A and 10B are intended to represent only a subset of the compounds contemplated herein as will be appreciated by a person of ordinary skill in the art and may have more or fewer amino acid residues.

Preferably, the glycosulfopeptide comprises an O-glycan comprising a β1,6 linkage to GalNAc. In a particularly preferred embodiment of the present invention, the O-glycan of the glycosulfopeptide is core-2 based.

Example 10

To test whether the specific type of linkage to the GalNAc is important for binding of GSP-6 to immobilized sPS, a novel glycosulfopeptide that is isomeric in structure to GSP-6 was synthesized. This glycosulfopeptide, designated core-1 GSP-6 (FIG. 11), has sLe$^x$ on an extended core-1 based O-glycan (C1-O-sLe$^x$) rather than on a core-2 based (β1,6 linked) O-glycan. A key step in the synthesis of core-1-GSP-6 is the addition of GlcNAc in β1-3 linkage to the Gal residue in the core-1 O-glycan by a recombinant β1,3-GlcNAcT from *Neisseria meningitidis* IgtA (Blixt et al., *Glycobiology*, In Press, 1999). This glycopeptide was subsequently modified by the action of β1,4-GalT, α2,3-SialylT and α1,3-FucT to generate a glycopeptide which has sLe$^x$ on the extended core-1 O-glycan. This compound was converted to core-1 GSP-6 by action of TPST-1. Mass spectral analysis confirmed the predicted size of the final product.

Unexpectedly, core-1 GSP-6 did not bind to immobilized sPS. To confirm the presence of sLe$^x$ on the extended core-1 O-glycan, ELISAs were performed using 2H5, a monoclonal antibody that recognizes the sLe$^x$ determinant (Sawada et al., *Biochem. Biophys. res. Commun.*, 193:337–347, 1993). 2H5 bound to immobilized GP-6 and core-1 GP-6, but not to a control glycopeptide GP-2, which lacks sLe$^x$ (data not shown). This verifies the expression of sLe$^x$ determinants on core-1 GP-6. These results demonstrate that preferably the sLe$^x$ glycan is β1,6 linked for binding the glycosulfopeptide-6 to immobilized sPS.

Utility

The present invention provides a method for the treatment of a patient afflicted with inflammatory diseases wherein such disease states may be treated by the administration of an effective amount of a compound of the present invention to a patient in need thereof.

A therapeutically effective amount of a compound of the present invention refers to an amount which is effective in controlling or reducing the inflammatory response. The term "controlling" is intended to refer to all processes wherein there may be a slowing, interrupting, arresting, or stopping of the progression of the disease and does not necessarily indicate a total elimination of all disease symptoms.

The term "therapeutically effective amount" is further meant to define an amount resulting in the improvement of any parameters or clinical symptoms characteristic of the inflammatory response. The actual dose will be different for the various specific molecules, and will vary with the patient's overall condition, the seriousness of the symptoms, and counterindications.

As used herein, the term "subject" or "patient" refers to a warm blooded animal such as a mammal which is afflicted with a particular inflammatory disease state. It is understood that guinea pigs, dogs, cats, rats, mice, horses, cattle, sheep, and humans are examples of animals within the scope of the meaning of the term.

A therapeutically effective amount of the compound used in the treatment described herein can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

A therapeutically effective amount of the compositions of the present invention will generally contain sufficient active ingredient to deliver from about 0.1 μg/kg to about 50 mg/kg (weight of active ingredient/body weight of patient). Preferably, the composition will deliver at least 0.5 to 10 mg/kg, and more preferably at least 1 μg/kg to 1 mg/kg.

Practice of the method of the present invention comprises administering to a patient a therapeutically effective amount of the active ingredient(s), in any suitable systemic or local formulation, in an amount effective to deliver the dosages listed above. An effective, particularly preferred dosage of the glycosulfopeptide (for example GSP-6) for substantially inhibiting activated neutrophils is 1 μg/kg to 1 mg/kg. The dosage can be administered on a one-time basis, or (for example) from one to 5 times per day.

Preferred amounts and modes of administration are able to be determined by one skilled in the art. One skilled in the art of preparing formulations can readily select the proper form and mode of administration depending upon the particular characteristics of the compound selected the disease state to be treated, the stage of the disease, and other relevant circumstances using formulation technology known in the art, described for example in *Remington's Pharmaceutical Sciences*, latest edition, Mack Publishing Co.

Pharmaceutical compositions can be manufactured utilizing techniques known in the art. Typically the therapeutically effective amount of the compound will be admixed with a pharmaceutically acceptable carrier.

The compounds or compositions of the present invention may be administered by a variety of routes, for example, orally or parenterally (i.e. subcutaneously, intravenously, intramuscularly, intraperitoneally, or intratracheally).

For oral administration, the compounds can be formulated into solid or liquid preparations such as capsules, pills, tablets, lozenges, melts, powders, suspensions, or emulsions. Solid unit dosage forms can be capsules of the ordinary gelatin type containing for example, surfactants, lubricants and inert fillers such as lactose, sucrose, and cornstarch or they can be sustained release preparations.

In another embodiment, the compounds of this invention can be tabletted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, and buffers as are known in the art.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

As noted above, the compositions can also include an appropriate carrier. For topical use, any of the conventional excipients may be added to formulate the active ingredients into a lotion, ointment, powder, cream, spray, or aerosol. For surgical implantation, the active ingredients may be combined with any of the well-known biodegradable and bio-erodible carriers, such as polylactic acid and collagen formulations. Such materials may be in the form of solid implants, sutures, sponges, wound dressings, and the like. In any event, for local use of the materials, the active ingredients usually be present in the carrier or excipient in a weight ratio of from about 1:1000 to 1:20,000, but are not limited to ratios within this range. Preparation of compositions for local use are detailed in *Remington's Pharmaceutical Sciences*, latest edition, (Mack Publishing).

Additional pharmaceutical methods may be employed to control the duration of action. Controlled release preparations may be achieved through the use of polymers to complex or absorb the glycosulfopeptide described herein. The controlled delivery may be achieved by selecting appropriate macromolecules (for example, polyesters, polyamino acids, polyvinyl, pyrrolidone, ethylenevinylacetate, methylcellulose, carboxymethylcellulose, or protamine, sulfate) and the appropriate concentration of macromolecules as well as the methods of incorporation, in order to control release.

Another possible method useful in controlling the duration of action by controlled release preparations is incorporation of the glycosulfopeptide molecule or its functional derivatives into particles of a polymeric material such as polyesters, polyamino acids, hydrogels, poly(lactic acid), or ethylene vinylacetate copolymers.

Alternatively, instead of incorporating the GSP into polymeric particles, it is possible to entrap these materials in microcapsules prepared, for example, by coacervation techniques or by interfacial polymerization (for example, hydroxymethylcellulose or gelatine-microcapsules and poly-(methylmethacylate) microcapsules, respectively), in colloidal drug delivery systems (for example, liposomes, albumin, microspheres, microemulsions, nano-particles, and nanocapsules), or in macroemulsions. Such techniques are disclosed in the latest edition of *Remington's Pharmaceutical Sciences*.

U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A good review of known methods is by G. Gregoriadis, Chapter 14. "Liposomes", *Drug Carriers in Biology and Medicine*, pp. 287–341 (Academic Press, 1979). Microspheres formed of polymers or proteins are well known to those skilled in the art, and can be tailored for passage through the gastrointestinal tract directly into the blood stream. Alternatively, the agents can be incorporated and the microspheres, or composite of microspheres, implanted for slow release over a period of time, ranging from days to months. See, for example, U.S. Pat. Nos. 4,906,474, 4,925, 673, and 3,625,214.

When the composition is to be used as an injectable material, it can be formulated into a conventional injectable carrier. Suitable carriers include biocompatible and pharmaceutically acceptable phosphate buffered saline solutions, which are preferably isotonic.

The term "inflammation" is meant to include reactions of both the specific and non-specific defense systems. A specific defense system reaction is a specific immune system reaction response to an antigen. Examples of a specific defense system reaction include the antibody response to antigens such as rubella virus, and delayed-type hypersensitivity response mediated by T-cells (as seen, for example, in individuals who test "positive" in the Mantaux test).

A non-specific defense system reaction is an inflammatory response mediated by leukocytes incapable of immunological memory. Such cells include granulocytes, macrophages, neutrophils, etc. Examples of a non-specific defense system reaction include the immediate swelling at the site of a bee sting, the reddening and cellular infiltrate induced at the site of a burn and the collection of PMN leukocytes at sites of bacterial infection (e.g., pulmonary infiltrates in bacterial pneumonias, pus formation in abscesses).

Although the invention is particularly suitable for cases of acute inflammation, it also has utility for chronic inflammation. Types of inflammation that can be treated with the present invention include diffuse inflammation, traumatic inflammation, immunosuppression, toxic inflammation, specific inflammation, reactive inflammation, parenchymatous inflammation, obliterative inflammation, interstitial inflammation, croupous inflammation, and focal inflammation.

It will be appreciated that the present invention will be easily adapted to the diagnosis, monitoring, and treatment of inflammatory disease processes such as rheumatoid arthritis, acute and chronic inflammation, post-ischemic (reperfusion) leukocyte-mediated tissue damage, acute leukocyte-mediated lung injury (e.g., Adult Respiratory Distress Syndrome), and other tissue-or organ-specific forms of acute inflammation (e.g., glomerulonephritis).

For reconstitution of a lyophilized product in accordance with this invention, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the Food and Drug Administration, which are available to those in the field.

The pharmaceutical composition may also be in the form of an aqueous solution containing many of the same substances as described above for the reconstitution of a lyophilized product.

The compounds can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

As mentioned above, the products of the invention may be incorporated into pharmaceutical preparations which may be used for therapeutic purposes. However, the term "pharmaceutical preparation" is intended in a broader sense herein to include preparations containing a glycosulfopeptide composition in accordance with this invention, used not only for therapeutic purposes but also for reagent or diagnostic purposes as known in the art, or for tissue culture. The pharmaceutical preparation intended for therapeutic use should contain a "pharmaceutically acceptable" or "therapeutically effective amount" of a GSP, i.e., that amount necessary for preventative or curative health measures. If the pharmaceutical preparation is to be employed as a reagent or diagnostic, then it should contain reagent or diagnostic amounts of a GSP.

Other Utilities

The present invention further comprises a method of producing oligosaccharides. In this method a glycopeptide is synthesized as described previously herein. The glycopeptide is subjected to a β-elimination reaction which causes the cleavage of the linkage between the glycan and the amino acid residue on the peptide to which the glycan was attached thereby producing the free oligosaccharide or glycan. In one version, for example, the β-elimination reaction comprises treating the glycopeptide with 50 mM NaOH and 1 M sodium borohydride at 50° C. for 16 hours. These oligosaccharides can be used, for example, as standards in other analyses.

Another utility of the glycosulfopeptides produced herein is to use specific GSPs with ELISA techniques to enable one to distinguish between monoclonal antibodies which react with core-2 sialyl Lewis$^x$ groups versus those which react with core-1 sialyl Lewis$^x$ groups.

Thus identified, the monoclonal antibodies can be used to characterize epitopes on glycoproteins, for example, to define glycoproteins which have core-2 SLe$^x$ groups versus those which have core-1-SLe$^x$ groups.

Another utility of the GSPs synthesized herein is that the GSPs are excellent acceptors for specific glycosyltransferases. This enables one to assay tissues for the presence therein of specific glycosyltransferases or sulfotransferases.

Another utility of the GSPs synthesized herein is to assay tissues for specific glycosidases which cause release of glycosyl or sulfo groups. HPLC is used to determine whether or not specific GSPs were altered in the assay, thereby indicating the presence or absence of particular glycosidases in the tissue sample.

The present invention may further comprise a method of inhibiting the binding of cells to a selectin comprising exposing the selectin to the a glycosulfopeptide compound described herein in an amount sufficient to bind to a cell binding site on the selectin.

All of the assay methods listed herein are well within the ability of one of ordinary skill in the art given the teachings provided herein.

All references cited herein are hereby incorporated herein in their entirety by reference.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

Changes may be made in the formulation and the use of the various compositions described herein or in the steps or the sequence of steps of the methods described herein without departing from the scope of the invention as defined in the following claims.

KEY TO ABBREVIATIONS

UDPGalNAc=Uridinediphospho N-acetylgalactosamine;
α-GalNAcT=UDPGalNAc:Ser/Thr αN-acetylgalactosaminyltransferase;
UDPGal=uridinediphospho galactose;
β1,3-GalT=UDPGal:GalNAcα1-Ser/Thr β1,3-galactosyltransferase;
UDPGlcNAc=Uridinephospho N-acetylglucosamine;
β1,6-GlcNAcT=UDPGlcNAc:Galβ1-3GalNAcα1-Ser/Thr (GlcNAc to GalNAc) β1,6-N-acetylglycosaminyltransferase;
β1,4-GalT=UDPGal:GlcNAc β1,4-galactosyltransferase;
CMPNeuAc=Cytosinemonophospho N-acetylneuraminic acid;
α2,3-ST=CMPNeuAc:Galβ1-4GlcNAc (NeuAc to Gal) α2,3-sialyltransferase;
GDPFuc=Guanosinediphospho Fucose;
α1,3-FT=GDPFuc:(+/-NeuAcα1-3)Galβ1-4GlcNAc (Fuc to GlcNAc) α1,3-fucosyltransferase;
PAPSulfate=Phosphoadenosinephosphosulfate;
TPST=Tyrosylprotein sulfotransferase

---

What is claimed is:

1. A process for making a glycosulfopeptide compound, comprising:
    (a) providing a presynthesized peptide comprising at least one tyrosine residue and at least one amino acid residue having a GalNAc side group linked thereto via an N- or O-linkage, respectively;
    (b) providing a purified core 1 β1,3-galactosyltransferase and enzymatically linking a Gal to the GalNAc via the core 1 β1,3-galactosyltransferase;
    (c) enzymatically linking a GlcNAc to the GalNAc via a N-acetylglucosaminyltransferase;
    (d) enzymatically linking a second Gal to the GlcNAc via a β1,4-galactosyltransferase;
    (e) enzymatically linking a sialic acid to the second Gal via an α2,3-sialyltransferase;
    (f) enzymatically linking a Fuc to the GlcNAc via an α1,3-fucosyltransferase; and
    (g) enzymatically linking a sulfate to the tyrosine residue via a tyrosylprotein sulfotransferase.

2. The method of claim 1 wherein the amino acid to which the GalNAc side group is attached is an O-linking amino acid.

3. The method of claim 2 wherein the O-linking amino acid is a serine or a threonine.

4. The method of claim 1 wherein the amino acid to which the GalNAc side group is attached is an N-linking amino acid.

5. The method of claim 1 wherein the GalNAc was linked enzymatically to the O-linking, or N-linking, amino acid residue via an N-acetyl-galactosaminyltransferase.

6. The method of claim 2 wherein the GalNAc was linked to the O-linking amino acid residue by chemically linking an acetylated GalNAc thereto wherein the acetylated GalNAc was then deacetylated.

7. The method of claim 1 wherein step (g) occurs immediately after any one of steps (a)–(f).

8. The method of claim 1 wherein the sialic acid is neuraminic acid.

9. The method of claim 1 wherein in step (c) the GlcNAc is linked to the GalNAc via a β_1,6 linkage.

10. A process for making a glycosulfopeptide, comprising:
    providing a presynthesized peptide comprising at least one tyrosine residue and at least one O-linking amino acid residue having a GalNAc linked thereto, then linking a Gal to the GalNAc via a core 1 βα1,3-galactosyltransferase, linking a GlcNAc to the GalNAc via a N-acetylglucosaminyltransferase, linking a second Gal to the GlcNAc via a βα1,4-galactosyltransferase, linking a sialic acid to the second Gal via an αα2,3-sialyltransferase, linking a Fuc to the GlcNAc via an αα1,3-fucosyltransferase, and linking a sulfate to the tyrosine residue via a tyrosylprotein sulfotransferase.

11. A process for making a glycosulfopeptide, comprising:
    providing a presynthesized peptide comprising at least one tyrosine residue and at least one N-linking amino acid residue having a GalNAc linked thereto, then linking a Gal to the GalNAc via a core 1 βα1,3-galactosyltransferase, linking a GlcNAc to the GalNAc via a N-acetylglucosaminyltransferase, linking a second Gal to the GlcNAc via a β1,4-galactosyltransferase, linking a sialic acid to the second Gal via an α2,3 sialyltransferase, linking a Fuc to the GlcNAc via an αα1,3-fucosyltransferase, and linking a sulfate to the tyrosine residue via a tyrosylprotein sulfotransferase.

12. A process for making a glycosulfopeptide, comprising:
    providing a presynthesized peptide comprising at least one tyrosine residue, and at least one O-linking amino acid residue having a GalNAc linked thereto, then linking a Gal to the GalNAc via a galactosyltransferase able to form a core 1 Gal βα1,3-GalNAc structure, linking a GlcNAc to the GalNAc via a N-acetylglucosaminyltransferase, linking a second Gal to the GlcNAc via a βα1,4-galactosyltransferase, linking a sialic acid to the second Gal via an αα2,3-sialyltransferase, linking a Fuc to the GlcNAc via an α1,3-fucosyltransferase, and linking a sulfate to the tyrosine residue via a tyrosylprotein sulfotransferase.

13. A process for making a glycosulfopeptide, comprising:

providing a presynthesized peptide comprising at least one tyrosine residue, and at least one N-linking amino acid residue having a GalNAc linked thereto, then linking a Gal to the GalNAc via a galactosyltransferase able to form a core 1 Gal $\beta\alpha 1,3$ GalNAc structure, linking a GlcNAc to the GalNAc via a N-acetylglucosaminyltransferase, linking a second Gal to the GlcNAc via a $\beta\alpha 1,4$-galactosyltransferase, linking a sialic acid to the second Gal via an $\alpha\alpha 2,3$-sialyltransferase, linking a Fuc to the GlcNAc via an $\alpha 1,3$-fucosyltransferase, and linking a sulfate to the tyrosine residue via a tyrosylprotein sulfotransferase.

* * * * *

UNITED STATES PATENT AND TRADEMARK OFFICE
CERTIFICATE OF CORRECTION

PATENT NO.   : 6,569,998 B2
DATED        : May 27, 2003
INVENTOR(S)  : Richard D. Cummings et al.

It is certified that error appears in the above-identified patent and that said Letters Patent is hereby corrected as shown below:

Column 10,
Lines 33 and 45, "1 βα1,3" and substitute therefore -- 1 β 1,3 --.
Lines 36 and 63, "βα1,4" and substitute therefore -- β 1,4 --.
Lines 38 and 64, "αα2,3" and substitute therefore -- α 2,3 --.
Lines 39 and 51, "αα1,3" and substitute therefore -- α 1,3 --.
Line 60, delete "βα1,3" and substitute therefore -- β 1,3 --.

Column 49,
Line 7, delete "βα1,3" and substitute therefore -- β 1,3 --.

Column 50,
Line 2, delete "βα1,4" and substitute therefore -- β 1,4 --.
Line 3, delete "αα2,3" and substitute therefore -- α 2,3 --.

Signed and Sealed this

Fifteenth Day of June, 2004

JON W. DUDAS
*Acting Director of the United States Patent and Trademark Office*

SEQUENCE LISTING

```
<160> NUMBER OF SEQ ID NOS: 40

<210> SEQ ID NO 1
<211> LENGTH: 363
<212> TYPE: PRT
<213> ORGANISM: Homo sapiens

<400> SEQUENCE: 1

Met Ala Ser Lys Ser Trp Leu Asn Phe Leu Thr Phe Leu Cys Gly Ser
1               5                   10                  15

Ala Ile Gly Phe Leu Leu Cys Ser Gln Leu Phe Ser Ile Leu Leu Gly
            20                  25                  30

Glu Lys Val Asp Thr Gln Pro Asn Val Leu His Asn Asp Pro His Ala
        35                  40                  45

Arg His Ser Asp Asp Asn Gly Gln Asn His Leu Glu Gly Gln Met Asn
    50                  55                  60

Phe Asn Ala Asp Ser Ser Gln His Lys Asp Glu Asn Thr Asp Ile Ala
65                  70                  75                  80

Glu Asn Leu Tyr Gln Lys Val Arg Ile Leu Cys Trp Val Met Thr Gly
                85                  90                  95

Pro Gln Asn Leu Glu Lys Lys Ala Lys His Val Lys Ala Thr Trp Ala
            100                 105                 110

Gln Arg Cys Asn Lys Val Leu Phe Met Ser Ser Glu Glu Asn Lys Asp
```

-continued

```
                115                 120                 125
    Phe Pro Ala Val Gly Leu Lys Thr Lys Glu Gly Arg Asp Gln Leu Tyr
            130                 135                 140
Trp Lys Thr Ile Lys Ala Phe Gln Tyr Val His Glu His Tyr Leu Glu
145                 150                 155                 160
Asp Ala Asp Trp Phe Leu Lys Ala Asp Asp Thr Tyr Val Ile Leu
                165                 170                 175
Asp Asn Leu Arg Trp Leu Leu Ser Lys Tyr Asp Pro Glu Glu Pro Ile
            180                 185                 190
Tyr Phe Gly Arg Arg Phe Lys Pro Tyr Val Lys Gln Gly Tyr Met Ser
            195                 200                 205
Gly Gly Ala Gly Tyr Val Leu Ser Lys Glu Ala Leu Lys Arg Phe Val
210                 215                 220
Asp Ala Phe Lys Thr Asp Lys Cys Thr His Ser Ser Ile Glu Asp
225                 230                 235                 240
Leu Ala Leu Gly Arg Cys Met Glu Ile Met Asn Val Glu Ala Gly Asp
                245                 250                 255
Ser Arg Asp Thr Ile Gly Lys Glu Thr Phe His Pro Phe Val Pro Glu
            260                 265                 270
His His Leu Ile Lys Gly Tyr Leu Pro Arg Thr Phe Trp Tyr Trp Asn
            275                 280                 285
Tyr Asn Tyr Tyr Pro Pro Val Glu Gly Pro Gly Cys Cys Ser Asp Leu
290                 295                 300
Ala Val Ser Phe His Tyr Val Asp Ser Thr Thr Met Tyr Glu Leu Glu
305                 310                 315                 320
Tyr Leu Val Tyr His Leu Arg Pro Tyr Gly Tyr Leu Tyr Arg Tyr Gln
                325                 330                 335
Pro Thr Leu Pro Glu Arg Ile Leu Lys Glu Ile Ser Gln Ala Asn Lys
            340                 345                 350
Asn Glu Asp Thr Lys Val Lys Leu Gly Asn Pro
            355                 360

<210> SEQ ID NO 2
<211> LENGTH: 370
<212> TYPE: PRT
<213> ORGANISM: Homo sapiens

<400> SEQUENCE: 2

Met Val Gly Lys Leu Lys Gln Asn Leu Leu Ala Cys Leu Val Ile
1               5                   10                  15
Ser Ser Val Thr Val Phe Tyr Leu Gly Gln His Ala Met Glu Cys His
                20                  25                  30
His Arg Ile Glu Glu Arg Ser Gln Pro Val Lys Leu Glu Ser Thr Arg
            35                  40                  45
Thr Thr Val Arg Thr Gly Leu Asp Leu Lys Ala Asn Lys Thr Phe Ala
        50                  55                  60
Tyr His Lys Asp Met Pro Leu Ile Phe Ile Gly Val Pro Arg Ser
65                  70                  75                  80
Gly Thr Thr Leu Met Arg Ala Met Leu Asp Ala His Pro Asp Ile Arg
                85                  90                  95
Cys Gly Glu Glu Thr Arg Val Ile Pro Arg Ile Leu Ala Leu Lys Gln
            100                 105                 110
Met Trp Ser Arg Ser Ser Lys Glu Lys Ile Arg Leu Asp Glu Ala Gly
            115                 120                 125
```

```
Val Thr Asp Glu Val Leu Asp Ser Ala Met Gln Ala Phe Leu Leu Glu
    130                 135                 140

Ile Ile Val Lys His Gly Glu Pro Ala Pro Tyr Leu Cys Asn Lys Asp
145                 150                 155                 160

Pro Phe Ala Leu Lys Ser Leu Thr Tyr Leu Ser Arg Leu Phe Pro Asn
                165                 170                 175

Ala Lys Phe Leu Leu Met Val Arg Asp Gly Arg Ala Ser Val His Ser
            180                 185                 190

Met Ile Ser Arg Lys Val Thr Ile Ala Gly Phe Asp Leu Asn Ser Tyr
        195                 200                 205

Arg Asp Cys Leu Thr Lys Trp Asn Arg Ala Ile Glu Thr Met Tyr Asn
    210                 215                 220

Gln Cys Met Glu Val Gly Tyr Lys Lys Cys Met Leu Val His Tyr Glu
225                 230                 235                 240

Gln Leu Val Leu His Pro Glu Arg Trp Met Arg Thr Leu Leu Lys Phe
                245                 250                 255

Leu Gln Ile Pro Trp Asn His Ser Val Leu His His Glu Glu Met Ile
            260                 265                 270

Gly Lys Ala Gly Gly Val Ser Leu Ser Lys Val Glu Arg Ser Thr Asp
        275                 280                 285

Gln Val Ile Lys Pro Val Asn Val Gly Ala Leu Ser Lys Trp Val Gly
    290                 295                 300

Lys Ile Pro Pro Asp Val Leu Gln Asp Met Ala Val Ile Ala Pro Met
305                 310                 315                 320

Leu Ala Lys Leu Gly Tyr Asp Pro Tyr Ala Asn Pro Asn Tyr Gly
                325                 330                 335

Lys Pro Asp Pro Lys Ile Ile Glu Asn Thr Arg Arg Val Tyr Lys Gly
            340                 345                 350

Glu Phe Gln Leu Pro Asp Phe Leu Lys Glu Lys Pro Gln Thr Glu Gln
        355                 360                 365

Val Glu
    370

<210> SEQ ID NO 3
<211> LENGTH: 377
<212> TYPE: PRT
<213> ORGANISM: Homo sapiens

<400> SEQUENCE: 3

Met Arg Leu Ser Val Arg Arg Val Leu Leu Ala Ala Gly Cys Ala Leu
1               5                   10                  15

Val Leu Val Leu Ala Val Gln Leu Gly Gln Gln Val Leu Glu Cys Arg
            20                  25                  30

Ala Val Leu Ala Gly Leu Arg Ser Pro Arg Gly Ala Met Arg Pro Glu
        35                  40                  45

Gln Glu Glu Leu Val Met Val Gly Thr Asn His Val Glu Tyr Arg Tyr
    50                  55                  60

Gly Lys Ala Met Pro Leu Ile Phe Val Gly Val Pro Arg Ser Gly
65                  70                  75                  80

Thr Thr Leu Met Arg Ala Met Leu Asp Ala His Pro Glu Val Arg Cys
                85                  90                  95

Gly Glu Glu Thr Arg Ile Ile Pro Arg Val Leu Ala Met Arg Gln Ala
            100                 105                 110

Trp Ser Lys Ser Gly Arg Glu Lys Leu Arg Leu Asp Glu Ala Gly Val
        115                 120                 125
```

```
Thr Asp Glu Val Leu Asp Ala Ala Met Gln Ala Phe Ile Leu Glu Val
    130                 135                 140

Ile Ala Lys His Gly Glu Pro Ala Arg Val Leu Cys Asn Lys Asp Pro
145                 150                 155                 160

Phe Thr Leu Lys Ser Ser Val Tyr Leu Ser Arg Leu Phe Pro Asn Ser
                165                 170                 175

Lys Phe Leu Leu Met Val Arg Asp Gly Arg Ala Ser Val His Ser Met
            180                 185                 190

Ile Thr Arg Lys Val Thr Ile Ala Gly Phe Asp Leu Ser Ser Tyr Arg
        195                 200                 205

Asp Cys Leu Thr Lys Trp Asn Lys Ala Ile Glu Val Met Tyr Ala Gln
    210                 215                 220

Cys Met Glu Val Gly Lys Glu Lys Cys Leu Pro Val Tyr Tyr Glu Gln
225                 230                 235                 240

Leu Val Leu His Pro Arg Arg Ser Leu Lys Leu Ile Leu Asp Phe Leu
                245                 250                 255

Gly Ile Ala Trp Ser Asp Ala Val Leu His His Glu Asp Leu Ile Gly
            260                 265                 270

Lys Pro Gly Gly Val Ser Leu Ser Lys Ile Glu Arg Ser Thr Asp Gln
        275                 280                 285

Val Ile Lys Pro Val Asn Leu Glu Ala Leu Ser Lys Trp Thr Gly His
    290                 295                 300

Ile Pro Gly Asp Val Val Arg Asp Met Ala Gln Ile Ala Pro Met Leu
305                 310                 315                 320

Ala Gln Leu Gly Tyr Asp Pro Tyr Ala Asn Pro Pro Asn Tyr Gly Asn
                325                 330                 335

Pro Asp Pro Phe Val Ile Asn Asn Thr Gln Arg Val Leu Lys Gly Asp
            340                 345                 350

Tyr Lys Thr Pro Ala Asn Leu Lys Gly Tyr Phe Gln Val Asn Gln Asn
        355                 360                 365

Ser Thr Ser Ser His Leu Gly Ser Ser
    370                 375

<210> SEQ ID NO 4
<211> LENGTH: 48
<212> TYPE: DNA
<213> ORGANISM: Homo sapiens

<400> SEQUENCE: 4
gcctgaattt gtaagggatc cacacttaga gcttgctggg gagaatcc          48

<210> SEQ ID NO 5
<211> LENGTH: 72
<212> TYPE: DNA
<213> ORGANISM: Homo sapiens

<400> SEQUENCE: 5
gtagaattct tatcacttgc cgtcgatcag cctggggtcc acctggtcct cgtgttttaa   60
tgtctccaaa gc                                                       72

<210> SEQ ID NO 6
<211> LENGTH: 23
<212> TYPE: PRT
<213> ORGANISM: Artificial Sequence
<220> FEATURE:
<221> NAME/KEY: MISC_FEATURE
<222> LOCATION: (17)..(17)
```

```
<223> OTHER INFORMATION: threonine having a tetracetylated GalNAc
      linked thereto

<400> SEQUENCE: 6

Gly Gln Ala Thr Glu Tyr Glu Tyr Leu Asp Tyr Asp Phe Leu Pro Glu
1               5                   10                  15

Xaa Glu Pro Pro Glu Met Leu
            20

<210> SEQ ID NO 7
<211> LENGTH: 23
<212> TYPE: PRT
<213> ORGANISM: Artificial Sequence
<220> FEATURE:
<221> NAME/KEY: MISC_FEATURE
<222> LOCATION: (17)..(17)
<223> OTHER INFORMATION: threonine having a GalNAc linked thereto

<400> SEQUENCE: 7

Gly Gln Ala Thr Glu Tyr Glu Tyr Leu Asp Tyr Asp Phe Leu Pro Glu
1               5                   10                  15

Xaa Glu Pro Pro Glu Met Leu
            20

<210> SEQ ID NO 8
<211> LENGTH: 23
<212> TYPE: PRT
<213> ORGANISM: Artificial Sequence
<220> FEATURE:
<221> NAME/KEY: MISC_FEATURE
<222> LOCATION: (17)..(17)
<223> OTHER INFORMATION: threonine having a GalNAc disaccharide
      linked thereto

<400> SEQUENCE: 8

Gly Gln Ala Thr Glu Tyr Glu Tyr Leu Asp Tyr Asp Phe Leu Pro Glu
1               5                   10                  15

Xaa Glu Pro Pro Glu Met Leu
            20

<210> SEQ ID NO 9
<211> LENGTH: 23
<212> TYPE: PRT
<213> ORGANISM: Artificial Sequence
<220> FEATURE:
<221> NAME/KEY: MISC_FEATURE
<222> LOCATION: (17)..(17)
<223> OTHER INFORMATION: threonine having a Gal-GlcNAc-GalNAc
      trisaccharide linked thereto

<400> SEQUENCE: 9

Gly Gln Ala Thr Glu Tyr Glu Tyr Leu Asp Tyr Asp Phe Leu Pro Glu
1               5                   10                  15

Xaa Glu Pro Pro Glu Met Leu
            20

<210> SEQ ID NO 10
<211> LENGTH: 23
<212> TYPE: PRT
<213> ORGANISM: Artificial Sequence
<220> FEATURE:
<221> NAME/KEY: MISC_FEATURE
<222> LOCATION: (17)..(17)
<223> OTHER INFORMATION: threonine having a Gal-GlcNAc-Gal-GalNAc
      tetrasaccharide linked thereto

<400> SEQUENCE: 10
```

Gly Gln Ala Thr Glu Tyr Glu Tyr Leu Asp Tyr Asp Phe Leu Pro Glu
1               5                   10                  15

Xaa Glu Pro Pro Glu Met Leu
            20

<210> SEQ ID NO 11
<211> LENGTH: 23
<212> TYPE: PRT
<213> ORGANISM: Artificial Sequence
<220> FEATURE:
<221> NAME/KEY: MISC_FEATURE
<222> LOCATION: (17)..(17)
<223> OTHER INFORMATION: threonine having a NeuAc-Gal-GlcNAc-Gal-GalNAc
      pentasaccharide linked thereto

<400> SEQUENCE: 11

Gly Gln Ala Thr Glu Tyr Glu Tyr Leu Asp Tyr Asp Phe Leu Pro Glu
1               5                   10                  15

Xaa Glu Pro Pro Glu Met Leu
            20

<210> SEQ ID NO 12
<211> LENGTH: 23
<212> TYPE: PRT
<213> ORGANISM: Artificial Sequence
<220> FEATURE:
<221> NAME/KEY: MISC_FEATURE
<222> LOCATION: (17)..(17)
<223> OTHER INFORMATION: threonine having a NeuAc-Gal-Fuc-GlcNAc-Gal-
      GalNAc hexasaccharide linked thereto

<400> SEQUENCE: 12

Gly Gln Ala Thr Glu Tyr Glu Tyr Leu Asp Tyr Asp Phe Leu Pro Glu
1               5                   10                  15

Xaa Glu Pro Pro Glu Met Leu
            20

<210> SEQ ID NO 13
<211> LENGTH: 23
<212> TYPE: PRT
<213> ORGANISM: Artificial Sequence
<220> FEATURE:
<221> NAME/KEY: MISC_FEATURE
<222> LOCATION: (6)..(6)
<223> OTHER INFORMATION: tyrosine having a sulfate linked thereto
<221> NAME/KEY: MISC_FEATURE
<222> LOCATION: (8)..(8)
<223> OTHER INFORMATION: tyrosine having a sulfate linked thereto
<221> NAME/KEY: MISC_FEATURE
<222> LOCATION: (11)..(11)
<223> OTHER INFORMATION: tyrosine having a sulfate linked thereto
<221> NAME/KEY: MISC_FEATURE
<222> LOCATION: (17)..(17)
<223> OTHER INFORMATION: threonine having a NeuAc-Gal-Fuc-GlcNAc-Gal-
      GalNAc hexasaccharide linked thereto

<400> SEQUENCE: 13

Gly Gln Ala Thr Glu Xaa Glu Xaa Leu Asp Xaa Asp Phe Leu Pro Glu
1               5                   10                  15

Xaa Glu Pro Pro Glu Met Leu
            20

<210> SEQ ID NO 14
<211> LENGTH: 23
<212> TYPE: PRT
<213> ORGANISM: Artificial Sequence
<220> FEATURE:

```
<223> OTHER INFORMATION: :

<400> SEQUENCE: 14

Gly Gln Ala Thr Glu Tyr Glu Tyr Leu Asp Tyr Asp Phe Leu Pro Glu
1               5                  10                  15

Thr Glu Pro Pro Glu Met Leu
            20

<210> SEQ ID NO 15
<211> LENGTH: 23
<212> TYPE: PRT
<213> ORGANISM: Artificial Sequence
<220> FEATURE:
<221> NAME/KEY: MISC_FEATURE
<222> LOCATION: (6)..(6)
<223> OTHER INFORMATION: tyrosine having a sulfate linked thereto
<221> NAME/KEY: MISC_FEATURE
<222> LOCATION: (8)..(8)
<223> OTHER INFORMATION: tyrosine having a sulfate linked thereto
<221> NAME/KEY: MISC_FEATURE
<222> LOCATION: (11)..(11)
<223> OTHER INFORMATION: tyrosine having a sulfate linked thereto
<221> NAME/KEY: MISC_FEATURE
<222> LOCATION: (17)..(17)
<223> OTHER INFORMATION: threonine having a tetracetylated GalNAc
      linked thereto

<400> SEQUENCE: 15

Gly Gln Ala Thr Glu Xaa Glu Xaa Leu Asp Xaa Asp Phe Leu Pro Glu
1               5                  10                  15

Xaa Glu Pro Pro Glu Met Leu
            20

<210> SEQ ID NO 16
<211> LENGTH: 23
<212> TYPE: PRT
<213> ORGANISM: Artificial Sequence
<220> FEATURE:
<221> NAME/KEY: MISC_FEATURE
<222> LOCATION: (6)..(6)
<223> OTHER INFORMATION: tyrosine having a sulfate linked thereto
<221> NAME/KEY: MISC_FEATURE
<222> LOCATION: (8)..(8)
<223> OTHER INFORMATION: tyrosine having a sulfate linked thereto
<221> NAME/KEY: MISC_FEATURE
<222> LOCATION: (11)..(11)
<223> OTHER INFORMATION: tyrosine having a sulfate linked thereto
<221> NAME/KEY: MISC_FEATURE
<222> LOCATION: (17)..(17)
<223> OTHER INFORMATION: threonine having a GalNAc linked thereto

<400> SEQUENCE: 16

Gly Gln Ala Thr Glu Xaa Glu Xaa Leu Asp Xaa Asp Phe Leu Pro Glu
1               5                  10                  15

Xaa Glu Pro Pro Glu Met Leu
            20

<210> SEQ ID NO 17
<211> LENGTH: 23
<212> TYPE: PRT
<213> ORGANISM: Artificial Sequence
<220> FEATURE:
<221> NAME/KEY: MISC_FEATURE
<222> LOCATION: (6)..(6)
<223> OTHER INFORMATION: tyrosine having a sulfate linked thereto
<221> NAME/KEY: MISC_FEATURE
<222> LOCATION: (8)..(8)
<223> OTHER INFORMATION: tyrosine having a sulfate linked thereto
<221> NAME/KEY: MISC_FEATURE
<222> LOCATION: (11)..(11)
```

<223> OTHER INFORMATION: tyrosine having a sulfate linked thereto
<221> NAME/KEY: MISC_FEATURE
<222> LOCATION: (17)..(17)
<223> OTHER INFORMATION: threonine having a Gal-GalNAc disaccharide
      linked thereto

<400> SEQUENCE: 17

Gly Gln Ala Thr Glu Xaa Glu Xaa Leu Asp Xaa Asp Phe Leu Pro Glu
1               5                  10                  15

Xaa Glu Pro Pro Glu Met Leu
            20

<210> SEQ ID NO 18
<211> LENGTH: 23
<212> TYPE: PRT
<213> ORGANISM: Artificial Sequence
<220> FEATURE:
<221> NAME/KEY: MISC_FEATURE
<222> LOCATION: (6)..(6)
<223> OTHER INFORMATION: tyrosine having a sulfate linked thereto
<221> NAME/KEY: MISC_FEATURE
<222> LOCATION: (8)..(8)
<223> OTHER INFORMATION: tyrosine having a sulfate linked thereto
<221> NAME/KEY: MISC_FEATURE
<222> LOCATION: (11)..(11)
<223> OTHER INFORMATION: tyrosine having a sulfate linked thereto
<221> NAME/KEY: MISC_FEATURE
<222> LOCATION: (17)..(17)
<223> OTHER INFORMATION: threonine having a Gal-GlcNAc-GalNAc
      trisaccharide linked thereto

<400> SEQUENCE: 18

Gly Gln Ala Thr Glu Xaa Glu Xaa Leu Asp Xaa Asp Phe Leu Pro Glu
1               5                  10                  15

Xaa Glu Pro Pro Glu Met Leu
            20

<210> SEQ ID NO 19
<211> LENGTH: 23
<212> TYPE: PRT
<213> ORGANISM: Artificial Sequence
<220> FEATURE:
<221> NAME/KEY: MISC_FEATURE
<222> LOCATION: (6)..(6)
<223> OTHER INFORMATION: tyrosine having a sulfate linked thereto
<221> NAME/KEY: MISC_FEATURE
<222> LOCATION: (8)..(8)
<223> OTHER INFORMATION: tyrosine having a sulfate linked thereto
<221> NAME/KEY: MISC_FEATURE
<222> LOCATION: (11)..(11)
<223> OTHER INFORMATION: tyrosine having a sulfate linked thereto
<221> NAME/KEY: MISC_FEATURE
<222> LOCATION: (17)..(17)
<223> OTHER INFORMATION: threonine having a Gal-GlcNAc-Gal-GalNAc
      tetrasaccharide linked thereto

<400> SEQUENCE: 19

Gly Gln Ala Thr Glu Xaa Glu Xaa Leu Asp Xaa Asp Phe Leu Pro Glu
1               5                  10                  15

Xaa Glu Pro Pro Glu Met Leu
            20

<210> SEQ ID NO 20
<211> LENGTH: 23
<212> TYPE: PRT
<213> ORGANISM: Artificial Sequence
<220> FEATURE:
<221> NAME/KEY: MISC_FEATURE
<222> LOCATION: (6)..(6)
<223> OTHER INFORMATION: tyrosine having a sulfate linked thereto
<221> NAME/KEY: MISC_FEATURE
<222> LOCATION: (8)..(8)
<223> OTHER INFORMATION: tyrosine having a sulfate linked thereto
<221> NAME/KEY: MISC_FEATURE
<222> LOCATION: (11)..(11)
<223> OTHER INFORMATION: tyrosine having a sulfate linked thereto
<221> NAME/KEY: MISC_FEATURE
<222> LOCATION: (17)..(17)
<223> OTHER INFORMATION: threonine having a NeuAc-Gal-GlcNAc-Gal-GalNAc pentasacchride linked thereto

<400> SEQUENCE: 20

Gly Gln Ala Thr Glu Xaa Glu Xaa Leu Asp Xaa Asp Phe Leu Pro Glu
1               5                   10                  15

Xaa Glu Pro Pro Glu Met Leu
            20

<210> SEQ ID NO 21
<211> LENGTH: 23
<212> TYPE: PRT
<213> ORGANISM: Artificial Sequence
<220> FEATURE:
<221> NAME/KEY: MISC_FEATURE
<222> LOCATION: (6)..(6)
<223> OTHER INFORMATION: tyrosine having a sulfate linked thereto
<221> NAME/KEY: MISC_FEATURE
<222> LOCATION: (8)..(8)
<223> OTHER INFORMATION: tyrosine having a sulfate linked thereto
<221> NAME/KEY: MISC_FEATURE
<222> LOCATION: (11)..(11)
<223> OTHER INFORMATION: tyrosine having a sulfate linked thereto
<221> NAME/KEY: MISC_FEATURE
<222> LOCATION: (17)..(17)
<223> OTHER INFORMATION: threonine having a tetracetylated G.cNAc linked thereto

<400> SEQUENCE: 21

Gly Gln Ala Thr Glu Xaa Glu Xaa Leu Asp Xaa Asp Phe Leu Pro Glu
1               5                   10                  15

Xaa Glu Pro Pro Glu Met Leu
            20

<210> SEQ ID NO 22
<211> LENGTH: 23
<212> TYPE: PRT
<213> ORGANISM: Artificial Sequence
<220> FEATURE:
<221> NAME/KEY: MISC_FEATURE
<222> LOCATION: (6)..(6)
<223> OTHER INFORMATION: tyrosine having a sulfate linked thereto
<221> NAME/KEY: MISC_FEATURE
<222> LOCATION: (8)..(8)
<223> OTHER INFORMATION: tyrosine having a sulfate linked thereto
<221> NAME/KEY: MISC_FEATURE
<222> LOCATION: (11)..(11)
<223> OTHER INFORMATION: tyrosine having a sulfate linked thereto
<221> NAME/KEY: MISC_FEATURE
<222> LOCATION: (17)..(17)
<223> OTHER INFORMATION: threonine having a GlcNAc linked thereto

<400> SEQUENCE: 22

Gly Gln Ala Thr Glu Xaa Glu Xaa Leu Asp Xaa Asp Phe Leu Pro Glu
1               5                   10                  15

Xaa Glu Pro Pro Glu Met Leu
            20

<210> SEQ ID NO 23
<211> LENGTH: 23
<212> TYPE: PRT
<213> ORGANISM: Artificial Sequence

```
<220> FEATURE:
<221> NAME/KEY: MISC_FEATURE
<222> LOCATION: (6)..(6)
<223> OTHER INFORMATION: tyrosine having a sulfate linked thereto
<221> NAME/KEY: MISC_FEATURE
<222> LOCATION: (8)..(8)
<223> OTHER INFORMATION: tyrosine having a sulfate linked thereto
<221> NAME/KEY: MISC_FEATURE
<222> LOCATION: (11)..(11)
<223> OTHER INFORMATION: tyrosine having a sulfate linked thereto
<221> NAME/KEY: MISC_FEATURE
<222> LOCATION: (17)..(17)
<223> OTHER INFORMATION: threonine having a Gal-GalNAc disaccharide
      linked thereto

<400> SEQUENCE: 23

Gly Gln Ala Thr Glu Xaa Glu Xaa Leu Asp Xaa Asp Phe Leu Pro Glu
1               5                   10                  15

Xaa Glu Pro Pro Glu Met Leu
            20

<210> SEQ ID NO 24
<211> LENGTH: 23
<212> TYPE: PRT
<213> ORGANISM: Artificial Sequence
<220> FEATURE:
<221> NAME/KEY: MISC_FEATURE
<222> LOCATION: (6)..(6)
<223> OTHER INFORMATION: tyrosine having a sulfate linked thereto
<221> NAME/KEY: MISC_FEATURE
<222> LOCATION: (8)..(8)
<223> OTHER INFORMATION: tyrosine having a sulfate linked thereto
<221> NAME/KEY: MISC_FEATURE
<222> LOCATION: (11)..(11)
<223> OTHER INFORMATION: tyrosine having a sulfate linked thereto
<221> NAME/KEY: MISC_FEATURE
<222> LOCATION: (17)..(17)
<223> OTHER INFORMATION: threonine having a NeuAc-Gal-GlcNAc linked
      thereto

<400> SEQUENCE: 24

Gly Gln Ala Thr Glu Xaa Glu Xaa Leu Asp Xaa Asp Phe Leu Pro Glu
1               5                   10                  15

Xaa Glu Pro Pro Glu Met Leu
            20

<210> SEQ ID NO 25
<211> LENGTH: 23
<212> TYPE: PRT
<213> ORGANISM: Artificial Sequence
<220> FEATURE:
<221> NAME/KEY: MISC_FEATURE
<222> LOCATION: (6)..(6)
<223> OTHER INFORMATION: tyrosine having a sulfate linked thereto
<221> NAME/KEY: MISC_FEATURE
<222> LOCATION: (8)..(8)
<223> OTHER INFORMATION: tyrosine having a sulfate linked thereto
<221> NAME/KEY: MISC_FEATURE
<222> LOCATION: (11)..(11)
<223> OTHER INFORMATION: tyrosine having a sulfate linked thereto
<221> NAME/KEY: MISC_FEATURE
<222> LOCATION: (17)..(17)
<223> OTHER INFORMATION: threonine having a NeuAc-Gal-Fuc-GlcNAc
      linked thereto

<400> SEQUENCE: 25

Gly Gln Ala Thr Glu Xaa Glu Xaa Leu Asp Xaa Asp Phe Leu Pro Glu
1               5                   10                  15

Xaa Glu Pro Pro Glu Met Leu
            20
```

```
<210> SEQ ID NO 26
<211> LENGTH: 23
<212> TYPE: PRT
<213> ORGANISM: Artificial Sequence
<220> FEATURE:
<221> NAME/KEY: MISC_FEATURE
<222> LOCATION: (6)..(6)
<223> OTHER INFORMATION: tyrosine having a sulfate linked thereto
<221> NAME/KEY: MISC_FEATURE
<222> LOCATION: (8)..(8)
<223> OTHER INFORMATION: tyrosine having a sulfate linked thereto
<221> NAME/KEY: MISC_FEATURE
<222> LOCATION: (11)..(11)
<223> OTHER INFORMATION: tyrosine having a sulfate linked thereto
<221> NAME/KEY: MISC_FEATURE
<222> LOCATION: (17)..(17)
<223> OTHER INFORMATION: threonine having an oligosaccharide R group
      linked thereto

<400> SEQUENCE: 26

Gly Gln Ala Thr Glu Xaa Glu Xaa Leu Asp Xaa Asp Phe Leu Pro Glu
1               5                   10                  15

Xaa Glu Pro Pro Glu Met Leu
            20

<210> SEQ ID NO 27
<211> LENGTH: 23
<212> TYPE: PRT
<213> ORGANISM: Artificial Sequence
<220> FEATURE:
<221> NAME/KEY: MISC_FEATURE
<222> LOCATION: (6)..(6)
<223> OTHER INFORMATION: tyrosine having a sulfate linked thereto
<221> NAME/KEY: MISC_FEATURE
<222> LOCATION: (8)..(8)
<223> OTHER INFORMATION: tyrosine having a sulfate linked thereto
<221> NAME/KEY: MISC_FEATURE
<222> LOCATION: (17)..(17)
<223> OTHER INFORMATION: threonine having a oligosaccharide R group
      linked thereto

<400> SEQUENCE: 27

Gly Gln Ala Thr Glu Xaa Glu Xaa Leu Asp Tyr Asp Phe Leu Pro Glu
1               5                   10                  15

Xaa Glu Pro Pro Glu Met Leu
            20

<210> SEQ ID NO 28
<211> LENGTH: 23
<212> TYPE: PRT
<213> ORGANISM: Artificial Sequence
<220> FEATURE:
<221> NAME/KEY: MISC_FEATURE
<222> LOCATION: (6)..(6)
<223> OTHER INFORMATION: tyrosine having a sulfate linked thereto
<221> NAME/KEY: MISC_FEATURE
<222> LOCATION: (17)..(17)
<223> OTHER INFORMATION: threonine having an oligosaccharide R group
      linked thereto
<221> NAME/KEY: MISC_FEATURE
<222> LOCATION: (11)..(11)
<223> OTHER INFORMATION: tyrosine having a sulfate linked thereto

<400> SEQUENCE: 28

Gly Gln Ala Thr Glu Xaa Glu Tyr Leu Asp Xaa Asp Phe Leu Pro Glu
1               5                   10                  15

Xaa Glu Pro Pro Glu Met Leu
            20
```

<210> SEQ ID NO 29
<211> LENGTH: 23
<212> TYPE: PRT
<213> ORGANISM: Artificial Sequence
<220> FEATURE:
<221> NAME/KEY: MISC_FEATURE
<222> LOCATION: (8)..(8)
<223> OTHER INFORMATION: tyrosine having a sulfate linked thereto
<221> NAME/KEY: MISC_FEATURE
<222> LOCATION: (11)..(11)
<223> OTHER INFORMATION: tyrosine having a sulfate linked thereto
<221> NAME/KEY: MISC_FEATURE
<222> LOCATION: (17)..(17)
<223> OTHER INFORMATION: threonine having an oligosaccharide R group

<400> SEQUENCE: 29

Gly Gln Ala Thr Glu Tyr Glu Xaa Leu Asp Xaa Asp Phe Leu Pro Glu
1               5                   10                  15

Xaa Glu Pro Pro Glu Met Leu
            20

<210> SEQ ID NO 30
<211> LENGTH: 23
<212> TYPE: PRT
<213> ORGANISM: Artificial Sequence
<220> FEATURE:
<221> NAME/KEY: MISC_FEATURE
<222> LOCATION: (11)..(11)
<223> OTHER INFORMATION: tyrosine having a sulfate linked thereto
<221> NAME/KEY: MISC_FEATURE
<222> LOCATION: (17)..(17)
<223> OTHER INFORMATION: threonine having an oligosaccharide thereto

<400> SEQUENCE: 30

Gly Gln Ala Thr Glu Tyr Glu Tyr Leu Asp Xaa Asp Phe Leu Pro Glu
1               5                   10                  15

Xaa Glu Pro Pro Glu Met Leu
            20

<210> SEQ ID NO 31
<211> LENGTH: 23
<212> TYPE: PRT
<213> ORGANISM: Artificial Sequence
<220> FEATURE:
<221> NAME/KEY: MISC_FEATURE
<222> LOCATION: (17)..(17)
<223> OTHER INFORMATION: threonine having an oligosacharide R group
      linked thereto
<221> NAME/KEY: MISC_FEATURE
<222> LOCATION: (8)..(8)
<223> OTHER INFORMATION: tyrosine having a sulfate linked thereto

<400> SEQUENCE: 31

Gly Gln Ala Thr Glu Tyr Glu Xaa Leu Asp Tyr Asp Phe Leu Pro Glu
1               5                   10                  15

Xaa Glu Pro Pro Glu Met Leu
            20

<210> SEQ ID NO 32
<211> LENGTH: 23
<212> TYPE: PRT
<213> ORGANISM: Artificial Sequence
<220> FEATURE:
<221> NAME/KEY: MISC_FEATURE
<222> LOCATION: (6)..(6)
<223> OTHER INFORMATION: tyrosine having a sulfate linked thereto
<221> NAME/KEY: MISC_FEATURE
<222> LOCATION: (17)..(17)
<223> OTHER INFORMATION: threonine having an oligosaccharide R group
      linked thereto

<400> SEQUENCE: 32

Gly Gln Ala Thr Glu Xaa Glu Tyr Leu Asp Tyr Asp Phe Leu Pro Glu
1               5                   10                  15

Xaa Glu Pro Pro Glu Met Leu
            20

<210> SEQ ID NO 33
<211> LENGTH: 15
<212> TYPE: PRT
<213> ORGANISM: Artificial Sequence
<220> FEATURE:
<221> NAME/KEY: MISC_FEATURE
<222> LOCATION: (3)..(3)
<223> OTHER INFORMATION: tyrosine having a sulfate linked thereto
<221> NAME/KEY: MISC_FEATURE
<222> LOCATION: (5)..(5)
<223> OTHER INFORMATION: tyrosine having a sulfate linked thereto
<221> NAME/KEY: MISC_FEATURE
<222> LOCATION: (8)..(8)
<223> OTHER INFORMATION: tyrosine having a sulfate linked thereto
<221> NAME/KEY: MISC_FEATURE
<222> LOCATION: (14)..(14)
<223> OTHER INFORMATION: threonine having an oligosaccharide R group
      linked thereto

<400> SEQUENCE: 33

Gly Glu Xaa Glu Xaa Leu Asp Xaa Asp Phe Leu Pro Glu Xaa Glu
1               5                   10                  15

<210> SEQ ID NO 34
<211> LENGTH: 15
<212> TYPE: PRT
<213> ORGANISM: Artificial Sequence
<220> FEATURE:
<221> NAME/KEY: MISC_FEATURE
<222> LOCATION: (3)..(3)
<223> OTHER INFORMATION: tyrosine having a sulfate linked thereto
<221> NAME/KEY: MISC_FEATURE
<222> LOCATION: (5)..(5)
<223> OTHER INFORMATION: tyrosine having a sulfate linked thereto
<221> NAME/KEY: MISC_FEATURE
<222> LOCATION: (14)..(14)
<223> OTHER INFORMATION: threonine having an oligosaccharide R group
      linked thereto

<400> SEQUENCE: 34

Gly Glu Xaa Glu Xaa Leu Asp Tyr Asp Phe Leu Pro Glu Xaa Glu
1               5                   10                  15

<210> SEQ ID NO 35
<211> LENGTH: 15
<212> TYPE: PRT
<213> ORGANISM: Artificial Sequence
<220> FEATURE:
<221> NAME/KEY: MISC_FEATURE
<222> LOCATION: (3)..(3)
<223> OTHER INFORMATION: tyrosine having a sulfate linked thereto
<221> NAME/KEY: MISC_FEATURE
<222> LOCATION: (8)..(8)
<223> OTHER INFORMATION: tyrosine having a sulfate linked thereto
<221> NAME/KEY: MISC_FEATURE
<222> LOCATION: (14)..(14)
<223> OTHER INFORMATION: threonine having an oligosaccharide R group
      linked thereto

<400> SEQUENCE: 35

Gly Glu Xaa Glu Tyr Leu Asp Xaa Asp Phe Leu Pro Glu Xaa Glu
1               5                   10                  15

```
<210> SEQ ID NO 36
<211> LENGTH: 15
<212> TYPE: PRT
<213> ORGANISM: Artificial Sequence
<220> FEATURE:
<221> NAME/KEY: MISC_FEATURE
<222> LOCATION: (5)..(5)
<223> OTHER INFORMATION: tyrosine having a sulfate linked thereto
<221> NAME/KEY: MISC_FEATURE
<222> LOCATION: (8)..(8)
<223> OTHER INFORMATION: tyrosine having a sulfate linked thereto
<221> NAME/KEY: MISC_FEATURE
<222> LOCATION: (14)..(14)
<223> OTHER INFORMATION: threonine having an oligosaccharide R group
      linked thereto

<400> SEQUENCE: 36

Gly Glu Tyr Glu Xaa Leu Asp Xaa Asp Phe Leu Pro Glu Xaa Glu
1               5                   10                  15

<210> SEQ ID NO 37
<211> LENGTH: 15
<212> TYPE: PRT
<213> ORGANISM: Artificial Sequence
<220> FEATURE:
<221> NAME/KEY: MISC_FEATURE
<222> LOCATION: (8)..(8)
<223> OTHER INFORMATION: tyrosine having a sulfate linked thereto
<221> NAME/KEY: MISC_FEATURE
<222> LOCATION: (14)..(14)
<223> OTHER INFORMATION: threonine having an oligosaccharide R group
      linked thereto

<400> SEQUENCE: 37

Gly Glu Tyr Glu Tyr Leu Asp Xaa Asp Phe Leu Pro Glu Xaa Glu
1               5                   10                  15

<210> SEQ ID NO 38
<211> LENGTH: 15
<212> TYPE: PRT
<213> ORGANISM: Artificial Sequence
<220> FEATURE:
<221> NAME/KEY: MISC_FEATURE
<222> LOCATION: (5)..(5)
<223> OTHER INFORMATION: tyrosine having a sulfate linked thereto
<221> NAME/KEY: MISC_FEATURE
<222> LOCATION: (14)..(14)
<223> OTHER INFORMATION: threonine having an oligosaccharide R group
      linked thereto

<400> SEQUENCE: 38

Gly Glu Tyr Glu Xaa Leu Asp Tyr Asp Phe Leu Pro Glu Xaa Glu
1               5                   10                  15

<210> SEQ ID NO 39
<211> LENGTH: 15
<212> TYPE: PRT
<213> ORGANISM: Artificial Sequence
<220> FEATURE:
<221> NAME/KEY: MISC_FEATURE
<222> LOCATION: (3)..(3)
<223> OTHER INFORMATION: tyrosine having a sulfate linked thereto
<221> NAME/KEY: MISC_FEATURE
<222> LOCATION: (14)..(14)
<223> OTHER INFORMATION: threonine having an oligosaccharide R group
      linked thereto

<400> SEQUENCE: 39

Gly Glu Xaa Glu Tyr Leu Asp Tyr Asp Phe Leu Pro Glu Xaa Glu
1               5                   10                  15
```

```
-continued

<210> SEQ ID NO 40
<211> LENGTH: 23
<212> TYPE: PRT
<213> ORGANISM: Artificial Sequence
<220> FEATURE:
<221> NAME/KEY: MISC_FEATURE
<222> LOCATION: (6)..(6)
<223> OTHER INFORMATION: tyrosine having a sulfate linked thereto
<221> NAME/KEY: MISC_FEATURE
<222> LOCATION: (8)..(8)
<223> OTHER INFORMATION: tyrosine having a sulfate linked thereto
<221> NAME/KEY: MISC_FEATURE
<222> LOCATION: (11)..(11)
<223> OTHER INFORMATION: tyrosine having a sulfate linked thereto
<221> NAME/KEY: MISC_FEATURE
<222> LOCATION: (17)..(17)
<223> OTHER INFORMATION: threonine having a NeuAc-Gal-Fuc-GlcNAc-Gal-
      GalNAc hexasaccharide linked thereto

<400> SEQUENCE: 40

Gly Gln Ala Thr Glu Xaa Glu Xaa Leu Asp Xaa Asp Phe Leu Pro Glu
1               5                   10                  15

Xaa Glu Pro Pro Glu Met Leu
            20
```